(12) United States Patent
Yasuda et al.

(10) Patent No.: US 12,245,747 B2
(45) Date of Patent: Mar. 11, 2025

(54) IMAGING CONTROL DEVICE, IMAGING CONTROL METHOD, PROGRAM, AND IMAGING SYSTEM

(71) Applicant: SONY GROUP CORPORATION, Tokyo (JP)

(72) Inventors: Ryouhei Yasuda, Tokyo (JP); Takuro Noda, Tokyo (JP)

(73) Assignee: SONY GROUP CORPORATION, Tokyo (JP)

( * ) Notice: Subject to any disclaimer, the term of this patent is extended or adjusted under 35 U.S.C. 154(b) by 524 days.

(21) Appl. No.: 17/430,226

(22) PCT Filed: Mar. 16, 2020

(86) PCT No.: PCT/JP2020/011447
§ 371 (c)(1),
(2) Date: Aug. 11, 2021

(87) PCT Pub. No.: WO2020/196026
PCT Pub. Date: Oct. 1, 2020

(65) Prior Publication Data
US 2022/0160214 A1    May 26, 2022

(30) Foreign Application Priority Data
Mar. 28, 2019    (JP) .................................. 2019-063439

(51) Int. Cl.
*A61B 1/00*    (2006.01)
*A61B 1/005*    (2006.01)
(Continued)

(52) U.S. Cl.
CPC .......... *A61B 1/00147* (2013.01); *A61B 1/005* (2013.01); *A61B 1/045* (2013.01); *A61B 1/05* (2013.01)

(58) Field of Classification Search
CPC ..... A61B 1/00147; A61B 1/005; A61B 1/045; A61B 1/05; A61B 2034/2065;
(Continued)

(56) References Cited

U.S. PATENT DOCUMENTS 5,876,325 A    3/1999    Mizuno
11,478,133 B2 *    10/2022    Kasai .................. A61B 1/3132
(Continued)

FOREIGN PATENT DOCUMENTS

JP    2001-149301 A    6/2001
JP    2003-088532 A    3/2003
(Continued)

*Primary Examiner* — Tung T Vo
(74) *Attorney, Agent, or Firm* — Paratus Law Group, PLLC

(57) ABSTRACT

There is provided an imaging control device, an imaging control method, a program, and an imaging system that enable easy change of a direction in which an image of a subject is captured in a case where imaging is performed using an optical member whose observation optical axis is inclined with respect to a central axis. The imaging control device includes: a rotation axis setting unit that sets a rotation axis on the basis of a pivot point and a point of interest on the subject, the pivot point serving as a fulcrum of the rod-shaped optical member whose observation optical axis is inclined with respect to the central axis and being not positioned on the observation optical axis; and a posture control unit that rotates the optical member around the rotation axis. The present technology can be applied to, for example, an endoscope system.

20 Claims, 14 Drawing Sheets

(51) Int. Cl.
*A61B 1/045* (2006.01)
*A61B 1/05* (2006.01)

(58) Field of Classification Search
CPC ... A61B 2090/371; A61B 34/30; A61B 90/37; A61B 2034/301; A61B 1/00006; A61B 1/00009; A61B 1/00149; A61B 1/00179; G03B 17/561; G03B 37/005
USPC .......................................................... 348/45
See application file for complete search history.

(56) References Cited

U.S. PATENT DOCUMENTS

| | | | |
|---|---|---|---|
| 2017/0143442 A1* | 5/2017 | Tesar | H04N 23/63 |
| 2017/0196643 A1* | 7/2017 | Popovic | A61B 6/12 |
| 2017/0281286 A1* | 10/2017 | Braun | A61B 17/3462 |
| 2018/0368656 A1* | 12/2018 | Austin | A61B 1/045 |
| 2019/0105113 A1* | 4/2019 | Popovic | A61B 1/0016 |
| 2019/0239972 A1* | 8/2019 | Chassot | A61B 34/74 |
| 2019/0254773 A1* | 8/2019 | Goebel | A61B 17/3462 |
| 2019/0274524 A1* | 9/2019 | Nagao | A61B 1/00149 |
| 2020/0046208 A1* | 2/2020 | Kasai | A61B 1/3132 |
| 2020/0337534 A1* | 10/2020 | Popovic | A61B 1/00045 |
| 2021/0330407 A1* | 10/2021 | Chassot | B25J 9/1682 |
| 2021/0369351 A1* | 12/2021 | Kuroda | G02B 21/24 |
| 2023/0218365 A1* | 7/2023 | Arai | A61B 1/00149 |

FOREIGN PATENT DOCUMENTS

| | | |
|---|---|---|
| JP | 2018-075218 A | 5/2018 |
| WO | WO 2015/083459 A1 | 6/2015 |
| WO | WO-2016072059 A1 | 5/2016 |
| WO | WO-2017062393 A2 | 4/2017 |
| WO | WO-2018159155 A1 | 9/2018 |

* cited by examiner

IMAGING CONTROL DEVICE, IMAGING CONTROL METHOD, PROGRAM, AND IMAGING SYSTEM

CROSS REFERENCE TO PRIOR APPLICATION

This application is a National Stage Patent Application of PCT International Patent Application No. PCT/JP2020/011447 (filed on Mar. 16, 2020) under 35 U.S.C. § 371, which claims priority to Japanese Patent Application No. 2019-063439 (filed on Mar. 28, 2019), which are all hereby incorporated by reference in their entirety.

TECHNICAL FIELD

The present technology relates to an imaging control device, an imaging control method, a program, and an imaging system, and more particularly, to an imaging control device, an imaging control method, a program, and an imaging system suitable for use in a case where imaging is performed using an optical member whose observation optical axis is inclined with respect to a central axis.

BACKGROUND ART

Conventionally, an oblique-viewing endoscope capable of capturing an image at an angle inclined with respect to a central axis is used as an insertion unit of an endoscope system for insertion into a living body. In an endoscope system using the oblique-viewing endoscope, an image of a subject can be captured at another angle by rotating the oblique-viewing endoscope and changing an orientation of an observation window at a distal end of the oblique-viewing endoscope.

However, in a case where the oblique-viewing endoscope is simply rotated, a region of interest of a user (hereinafter, referred to as a region of interest) moves to an end portion of an image or Goes out of an angle of view, and the user may lose sight of the region of interest. Therefore, in a case of rotating the oblique-viewing endoscope, the user needs co carefully adjust the angle and the like of the oblique-viewing endoscope while checking the image so as not to lose sight of the region of interest.

In this regard, conventionally, there has been proposed a method of rotating the insertion unit so that the observation optical axis of the insertion unit draws a conical locus having a point on an affected part of a patient as a vertex (see, for example, Patent Document) 1).

CITATION LIST

Patent Document

Patent Document 1: Japanese Patent Application Laid-Open No. 2003-88532

SUMMARY OF THE INVENTION

Problems to be Solved by the Invention

However, in the method described in Patent Document 1, since it is necessary to adjust the position of an entire rotation mechanism in advance in accordance with the region of interest of the affected part of the patient, the region of interest cannot be easily changed.

The present technology has been made in view of such a situation, and enables easy change of a direction in which an image of a subject is captured in a case where imaging is performed using an optical member whose observation optical axis is inclined with respect to a central axis.

Solutions to Problems

An imaging control device according to a first aspect of the present technology includes: a rotation axis setting unit that sets a rotation axis on the basis of a pivot point and a point of interest on a subject, the pivot point serving as a fulcrum of a rod-shaped optical member whose observation optical axis is inclined with respect to a central axis and being not positioned on the observation optical axis; and a posture control unit that rotates the optical member around the rotation axis.

An imaging control method according to the first the present technology performed by an imaging control device includes: setting a rotation axis on the basis of a pivot point and a point of interest on a subject, the pivot point serving as a fulcrum of a rod-shaped optical member whose observation optical axis is inclined with respect to a central axis and being not positioned on the observation optical axis; and rotating the optical member around the rotation axis.

A program according to the first aspect of the present technology causes a computer to execute processing of: setting a rotation axis on the basis of a pivot point and a point of interest on a subject, the pivot point serving as a fulcrum of a rod-shaped optical member whose observation optical axis is inclined with respect to a central axis and being not positioned on the observation optical axis; and rotating the optical member around the rotation axis.

An imaging system according to a second aspect of the present technology includes: an imaging unit that includes a rod-shaped optical member whose observation optical axis is inclined with respect to a central axis; a rotation axis setting unit that sets a rotation axis on the basis of a pivot point and a point of interest on a subject, the pivot point serving as a fulcrum of the optical member and being not positioned on the observation optical axis; and a posture control unit that rotates the optical member around the rotation axis.

According to the first aspect of the present technology, the rotation axis is set on the basis of the pivot point that serves as a fulcrum of the rod-shaped optical member whose observation optical axis is inclined with respect to the central axis, and is not positioned on the observation optical axis, and the point of interest on the subject, and the optical member is rotated around the rotation axis.

According to the second aspect of the present technology, the rotation axis is set on the basis of the pivot point that serves as a fulcrum of a rod-shaped optical member of an imaging unit that includes the optical member whose observation optical axis is inclined with respect to the central axis, and is not positioned on the observation optical axis, and the point of interest on the subject, and the optical member is rotated around the rotation axis.

MODE FOR CARRYING OUT THE INVENTION

Hereinafter, modes for carrying out the present technology will be described. Descriptions will be provided in the following order.
1. Embodiment
2. Modified Examples
3. Others 1. Embodiment First, an embodiment of the present technology will be described with reference to FIGS. 1 to 10.
<Example of Configuration of Imaging System>.

Figure 1:
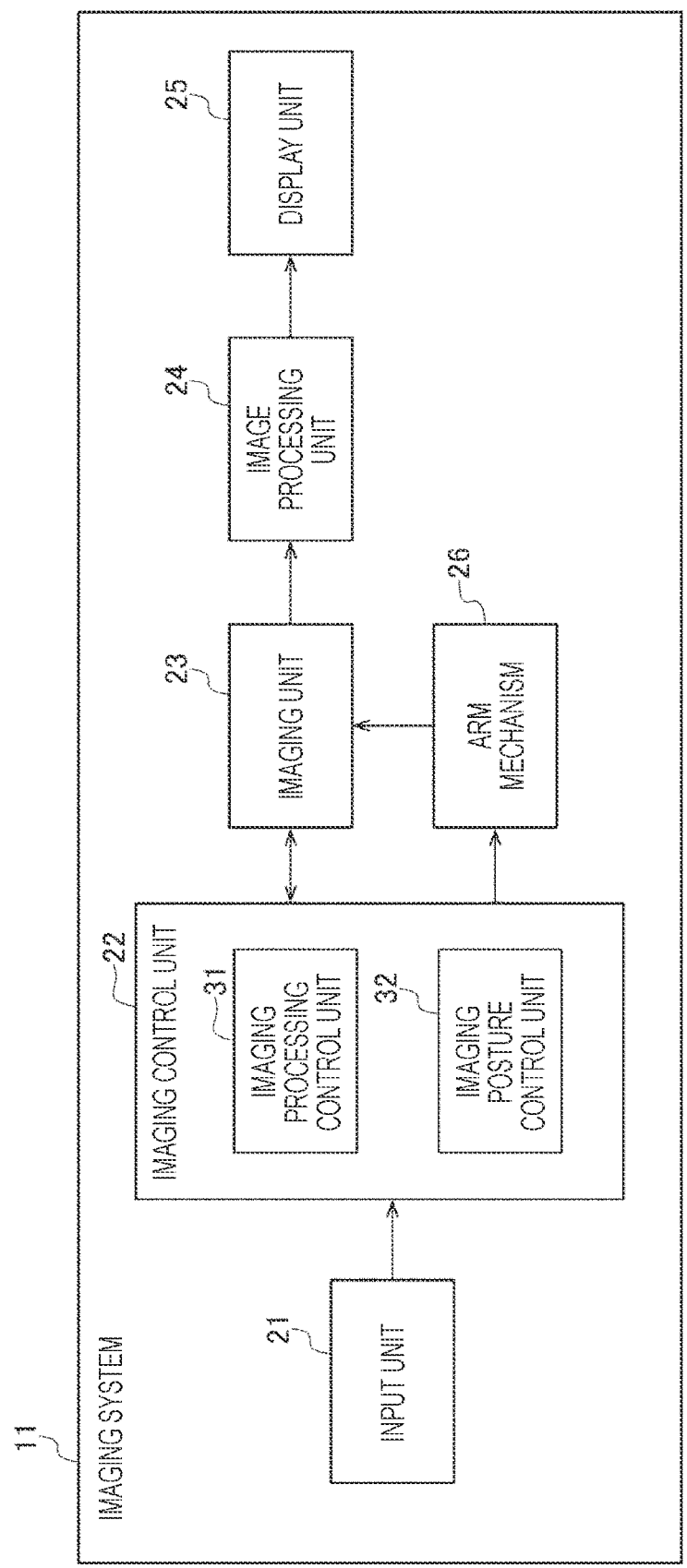
FIG. 1 is a block diagram illustrating an embodiment of an imaging system to which the present technology is applied.

FIG. 1 illustrates an example of a configuration of an imaging system 11 to which the present technology is applied.

The imaging system 11 is, for example, an endoscope system used in the medical field, and is used for imaging and observation in a living body. The imaging system 11 includes an input unit 21, an imaging control unit 22, an imaging unit 23, an image processing unit 24, a display unit 25, and an arm mechanism 26.

The input unit 21 includes an operation device such as a button, a switch, or a touch panel, and receives a user operation. The input unit 21 supplies an input signal input by the user operation to the imaging control unit 22.

The imaging control unit 22 controls imaging of a subject performed by the imaging unit 23. The imaging control unit 22 includes an imaging processing control unit 31 and an imaging posture control unit 32.

The imaging processing control unit 31 controls imaging processing (for example, an imaging timing or the like) of the imaging unit 23 and sets various imaging parameters and the like on the basis of the input signal supplied from the input unit 21, a captured image supplied from the imaging unit 23, and the like.

The imaging posture control unit 32 controls the imaging unit 23 and the arm mechanism 26 on the basis of the input signal supplied from the input unit 21, the captured image supplied from the imaging unit 23, and the like, thereby controlling the posture (hereinafter, referred to as an imaging posture) of the imaging unit 23. As a result, a position (hereinafter, referred to as an imaging position) and a direction (hereinafter, referred to as an imaging direction) at and in which the imaging unit 23 performs imaging are controlled.

The imaging unit 23 captures an image of the subject under the control of the imaging control unit 22. The imaging unit 23 supplies the image (hereinafter, referred to as a captured image) obtained by performing imaging to the imaging control unit 22 and the image processing unit 24.

The image processing unit 24 performs various types of image processing on the captured image, and supplies the captured image after the image processing to the display unit 25.

The display, unit 25 includes, for example, a display or the like. The display unit 25 displays an image based on the captured image. The image displayed on the display unit 25 is used as, for example, a monitor image for a doctor or the like to check an operative field or the like.

The arm mechanism 26 is implemented by, for example, a robot arm. The arm mechanism 26 supports the imaging unit 23 and changes the posture of the imaging unit 23 by moving the imaging unit 23 under the control of the imaging control unit 22.

<Example of Configuration of Imaging Unit 23>

Figure 2:
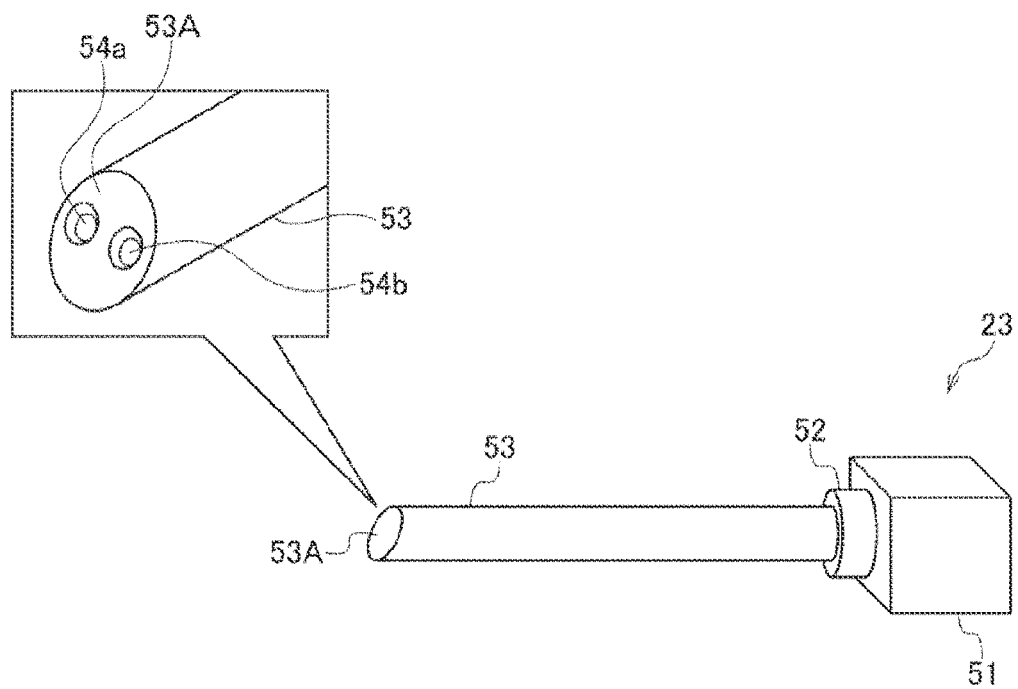
FIG. 2 is a schematic diagram illustrating an example of a configuration of an imaging unit.

FIG. 2 schematically illustrates an example of a configuration of the imaging unit 23 of FIG. 1.

The imaging unit 23 includes a camera 51, a rotary actuator 52, an insertion unit 53, and observation windows 54a and 54b. The camera 51 and the insertion unit 53 are connected via the rotary actuator 52. As illustrated in the enlarged view, the observation window 54a and the observation window 54b are provided in a distal end surface 53A of the insertion unit 53.

The camera 51 is implemented by, for example, an imaging device including an imaging element such as a complementary MOS (CMOS). The camera 51 captures an image of the subject by using light (hereinafter, referred to as subject light) from the subject incident via the insertion unit 53, and supplies the obtained captured image to the imaging control unit 22 and the image processing unit 24. Furthermore, the camera 51 includes, for example, two imaging elements (not illustrated), and can perform stereo imaging.

The rotary actuator 52 rotates the camera 51 around an optical axis (hereinafter, referred to as an imaging optical axis) of the camera 51 with respect to the insertion unit 53. That is, the camera 51 is provided at one end of the insertion unit 53 so as to be rotatable around the imaging optical axis via the rotary actuator 52. As the camera 51 is rotated around the imaging optical axis, a coordinate system of the camera 51 (hereinafter, referred to as a camera coordinate system) is rotated around the imaging optical axis.

Note that, hereinafter, an x axis of the camera coordinate system represents a lateral direction of the camera 51, a y axis represents a height direction of the camera 51, and a z axis represents a direction of the imaging optical axis.

The insertion unit 53 includes an optical system such as a lens or a mirror, and is a rod-shaped cylindrical optical member to be inserted into a living body. Note that the rod-shaped optical member includes a curved optical member and a linear optical member. Examples of the insertion unit 53 include an oblique-viewing endoscope implemented by a rigid endoscope.

The insertion unit 53 is connected to the camera 51 via the rotary actuator 52 so that a central axis thereof coincides with the imaging optical axis of the camera 51. The distal end surface 53A of the insertion unit 53 is inclined with respect to the central axis of the insertion unit 53, The distal end surface 53A of the insertion unit 53 is provided with the observation window 54a and the observation window 54b each implemented by a lens. The observation window 54a and the observation window 54b are laterally arranged at the same height in an inclination direction of the distal end surface 53A.

The subject light incident on the insertion unit 53 from each of the observation window 54a and the observation window 54b passes through the insertion unit 53 and is incident on a light receiving surface of each of different imaging elements of the camera 51. Then, the camera 51 captures a captured image (hereinafter, referred to as a left captured image) based on the subject light incident from the observation window 54a and captures a captured image (hereinafter, referred to as a right captured image) based on the subject light incident from the observation window 54b. That is, the camera 51 can perform stereo imaging. The camera 51 supplies the left captured image and the right captured image to the imaging control unit 22 and the image processing unit 24.

Here, an observation optical axis of the insertion unit 53, which is the optical axis of the observation window 54a and the observation window 54b, is perpendicular to the distal end surface 53A and inclined with respect to the central axis of the insertion unit 53. Therefore, the imaging unit 23 captures an image in an oblique direction with respect to the central axis of the insertion unit 53 via the insertion unit 53.

Note that, hereinafter, in a case where it is not necessary to individually distinguish the observation window 54a and the observation window 54b, they are simply referred to as the observation window 54. In addition, hereinafter, in a case where it is not necessary to distinguish the left captured image and the right captured image individually, they are simply referred to as the captured image.

<Example of Method of Inserting Insertion Unit 53>

Figure 3:
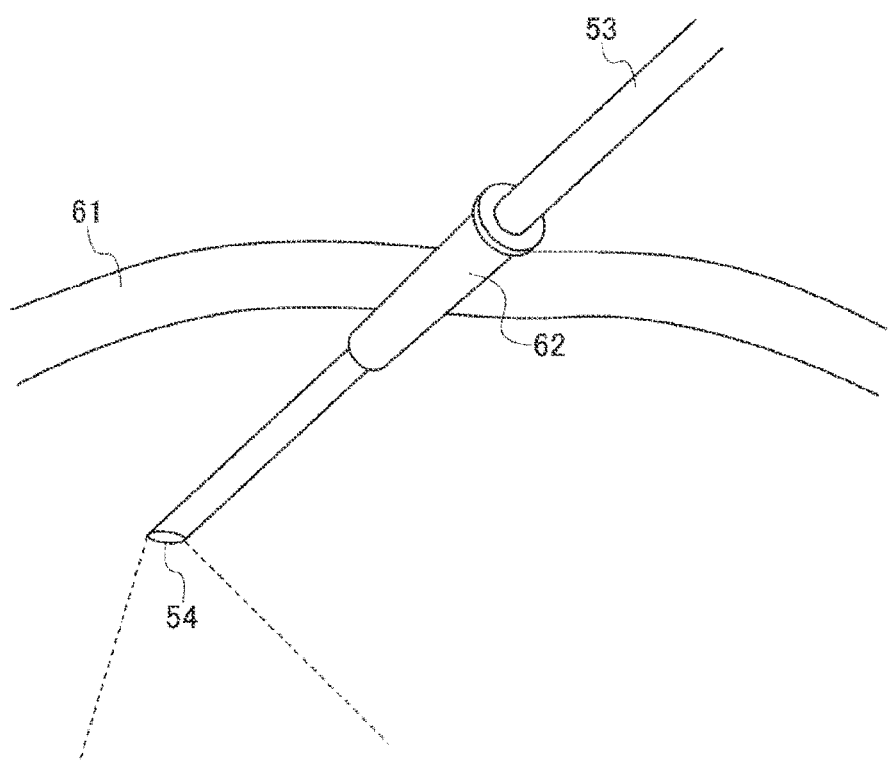
FIG. 3 is a diagram illustrating an example of a method of inserting an insertion unit into a living body.

FIG. 3 is a diagram illustrating an example of a method of inserting the insertion unit 53 into a living body.

In this example, the insertion unit 53 is inserted into the abdomen of the patient by using a trocar 62. Specifically, the trocar 62 is inserted into a skin 61 of the abdomen. Then, the insertion unit 53 is inserted from an insertion port of the trocar 62, and a distal end of the insertion unit 53 protrudes from a distal end port of the trocar 62. As a result, the insertion unit 53 is inserted into the living body, and the position of the insertion unit 53 is stabilized.

<Example of Configuration of Arm Mechanism 26>

Figure 4:
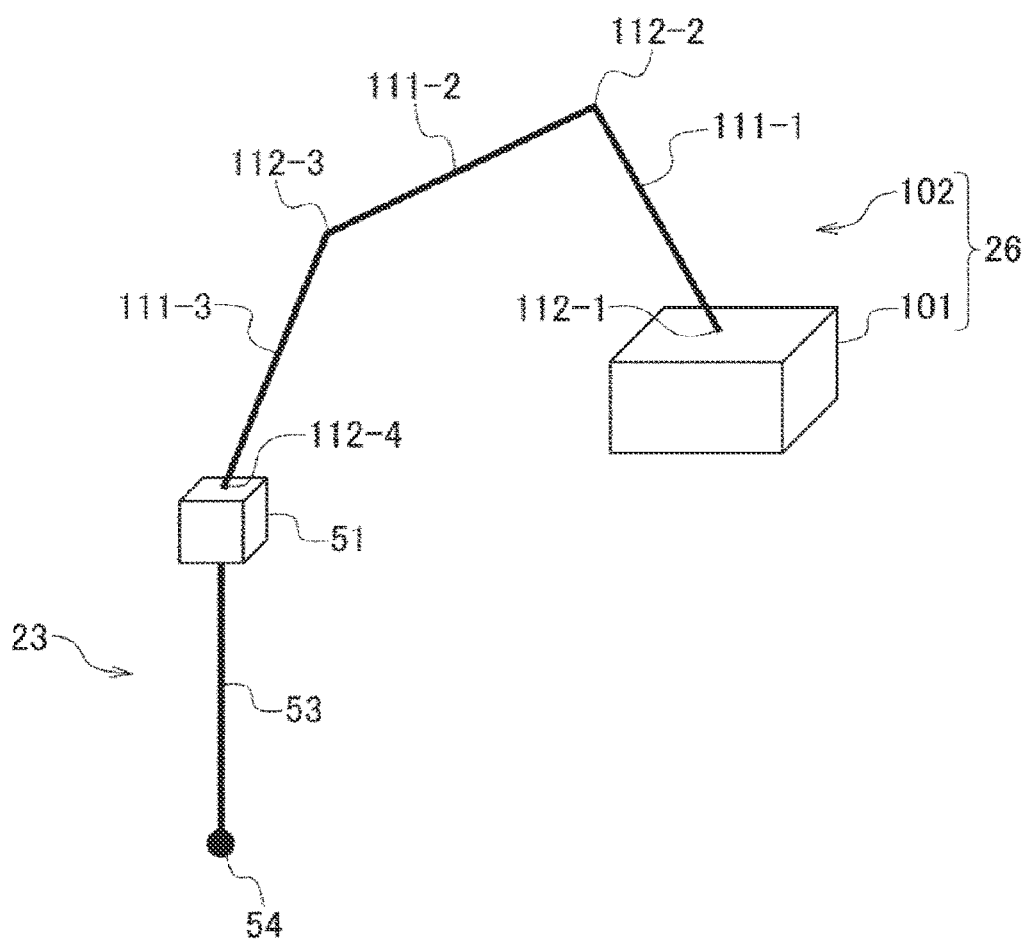
FIG. 4 is a schematic diagram illustrating an example of a configuration of an arm mechanism.

FIG. 4 schematically illustrates an example of a configuration of the arm mechanism 26 of FIG. 1. Note that, in FIG. 4, the imaging unit 23 is also schematically illustrated, and the rotary actuator 52 is not illustrated. Note that, also in the following similar drawings, the imaging unit 23 is basically schematically illustrated, and the rotary actuator 52 is not illustrated.

The arm mechanism 26 includes a base portion 101 and an arm portion 102. The arm portion 102 includes links 111-1 to 111-3 and joint portions 112-1 to 112-4. One end of the link 111-1 is connected to the base portion 101 via the joint portion 112-1, and the other end of the link 111-1 is connected to one end of the link 111-2 via the joint portion 112-2. The other end of the link 111-2 is connected to one end of the link 111-3 via the joint portion 112-3. The other end of the link 111-3 is connected to the camera 51 via the joint portion 112-4.

The base portion 101 supports, for example, the arm portion 102, has all or a part of the imaging control unit 22 of the imaging system 11 incorporated therein, and controls the movement of the arm portion 102.

The joint portions 112-1 to 112-4 are independently driven under the control of the imaging control unit 22. As a result, the posture of the arm portion 102 is changed, and the imaging posture is changed as the imaging unit 23 moves.

Note that, hereinafter, in a case where it is not necessary to individually distinguish the links 111-1 to 111-3, they are simply referred to as the link 111. Furthermore, hereinafter, in a case where it is not necessary to individually distinguish the joint portions 112-1 to 112-4, they are simply referred to as the joint portion 112.

<Example of Configuration of imaging Posture Control Unit 32>

Figure 5:
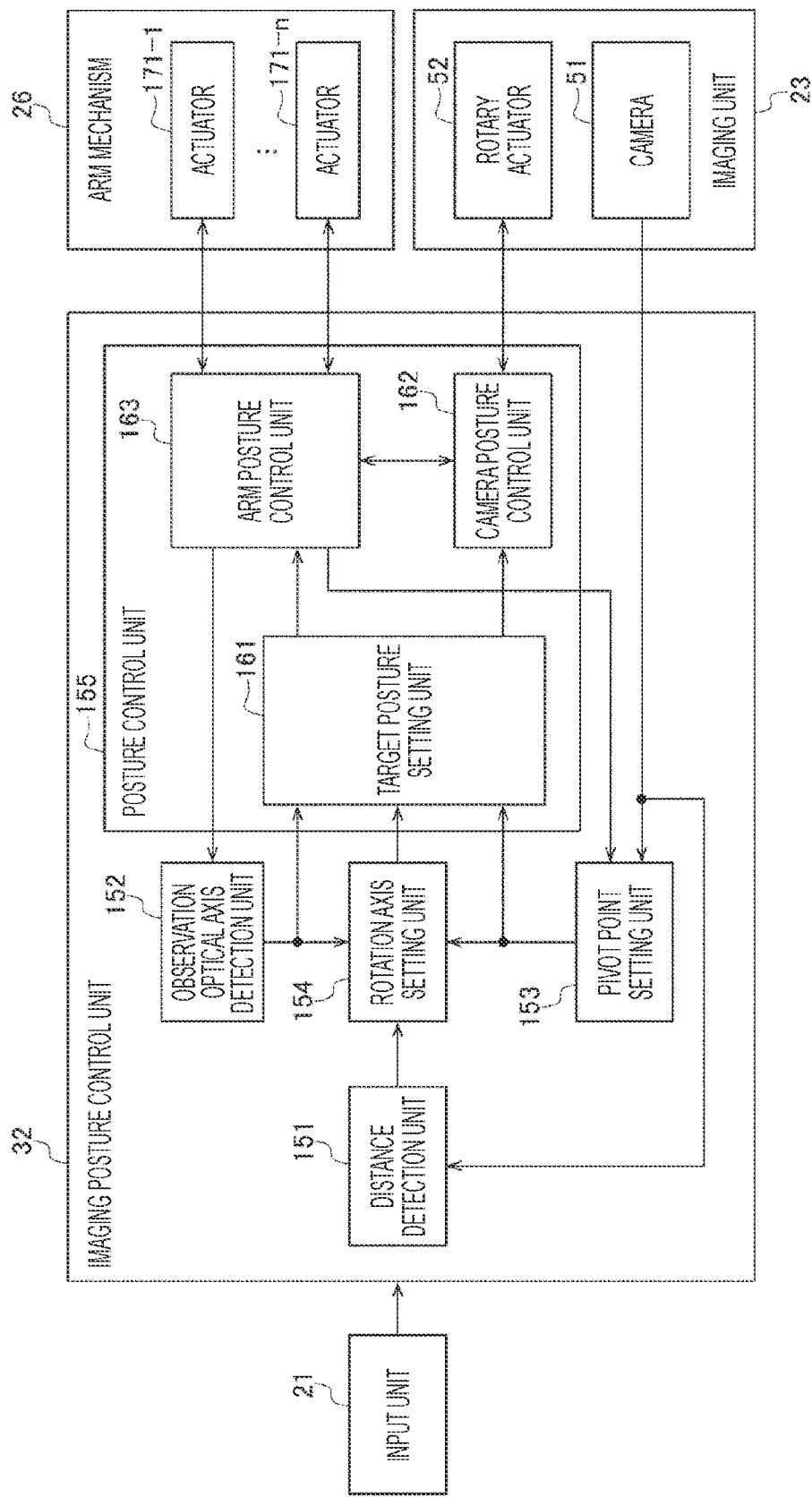
FIG. 5 is a block diagram illustrating an example of a configuration of functions of an imaging posture control unit.

FIG. 5 illustrates an example of a configuration of functions of the imaging posture control unit 32 of the imaging system 11 of FIG. 1.

The imaging posture control unit 32 includes a distance detection unit 151, an observation optical axis detection unit 152, a pivot point setting unit 153, a rotation axis setting unit 154, and a posture control unit 155. The posture control unit 155 includes a target posture setting unit 161, a camera posture control unit 162, and an arm posture control unit 163.

The distance detection unit 151 detects a distance to the subject on the basis of the left captured image and the right captured image supplied from the camera 51. For example, the distance detection unit 151 detects a distance between an arbitrary point (hereinafter, referred to as a point of interest) on the subject and the observation window 54. The distance detection unit 151 supplies data indicating a detection result to the rotation axis setting unit 154.

The observation optical axis detection unit 152 detects the posture (position and orientation) of the insertion unit 53 (in particular, the observation window 54) on the basis of data indicating the posture of the arm portion 102 (hereinafter, referred to as arm posture data) supplied from the arm posture control unit 163. In addition, the observation optical axis detection unit 152 detects the observation optical axis on the basis of the posture of the observation window 54. The observation optical axis detection unit 152 supplies data indicating a detection result to the rotation axis setting unit 154 and the target posture setting unit 161.

The pivot point setting unit 153 sets the position of a pivot point on the basis of the left captured image and the right captured image supplied from the camera 51 and the arm posture data supplied from the arm posture control unit 163. The pivot point is a point serving as a fulcrum in a case where the insertion unit 53 is rotated. The pivot point setting unit 153 supplies data indicating the position of the pivot point to the rotation axis setting unit 154 and the target posture setting unit 161.

The rotation axis setting unit 154 sets a rotation axis on the basis of a distance to the point of interest on the subject, the posture of the observation optical axis, and the position of the pivot point. This rotation axis is an axis around which the insertion unit 53 is rotated in a case of changing a direction in which an image of the subject is captured. The rotation axis setting unit 154 supplies data indicating the posture (position and orientation) of the rotation axis to the target posture setting unit 161.

In a case where the user performs an operation of changing the imaging posture via the input unit 21, the target posture setting unit 161 sets a target imaging posture (hereinafter, referred to as a target posture) on the basis of a content of the operation. In addition, the target posture setting unit 161 calculates the posture of the arm portion 102 (hereinafter, referred to as a target arm posture) and the posture of the camera 51 (hereinafter, referred to as a target camera posture) for realizing the target posture on the basis of the posture of the observation window 54, the posture of the observation optical axis, the position of the pivot point, the posture of the rotation axis, and the like. The target posture setting unit 161 supplies data indicating the target camera posture to the camera posture control unit 162. Furthermore, the target posture setting unit 161 supplies data indicating the target arm posture to the arm posture control unit 163.

The camera posture control unit 162 drives the rotary actuator 52 so that the camera 51 is in the target camera posture.

Furthermore, the camera posture control unit 162 detects the posture of the camera 51 on the basis of data indicating a rotation angle supplied from the rotary actuator 52. Note that the rotation angle of the rotary actuator 52 is detected using, for example, a potentiometer or the like included in the rotary actuator 52.

The arm posture control unit 163 drives actuators 171-1 to 171-*n* for driving the joint portions 112-1 to 112-4 of the arm portion 102 so that the arm portion 102 is in the target arm posture. Furthermore, the arm posture control unit 163 detects the posture of the arm portion 102 on the basis of data indicating rotation angles supplied from the actuators 171-1 to 171-*n*.

Note that the rotation angles of the actuators 171-1 to 171-*a* are detected using, for example, a potentiometer or the like included in each of the actuators 171-1 to 171-*n*.

Furthermore, hereinafter, in a case where it is not necessary to individually distinguish the actuators 171-1 to 171-*n*, they are simply referred to as the actuator 171.

<Imaging Direction Change Processing>

Next, imaging direction change processing performed by the imaging system 11 will be described with reference to a flowchart of FIG. 6.

Here, the imaging direction change processing is processing of changing the direction in which an image of the subject is captured, in particular, processing of changing the direction in which as image of a region of interest on the subject is captured.

For example, this processing starts once a power supply of the imaging system 11 is turned on, and ends once the power supply is turned off.

Note that examples illustrated in FIGS. 7 to 10 will be described as specific examples as appropriate.

In Step S1, the camera 51 starts imaging. Specifically, under the control of the imaging control unit 22, the camera 51 starts imaging and starts supplying a captured image to the imaging control unit 22 and the image processing unit 24.

In Step S2, the pivot point setting unit 153 sets the pivot point.

Figure 7:
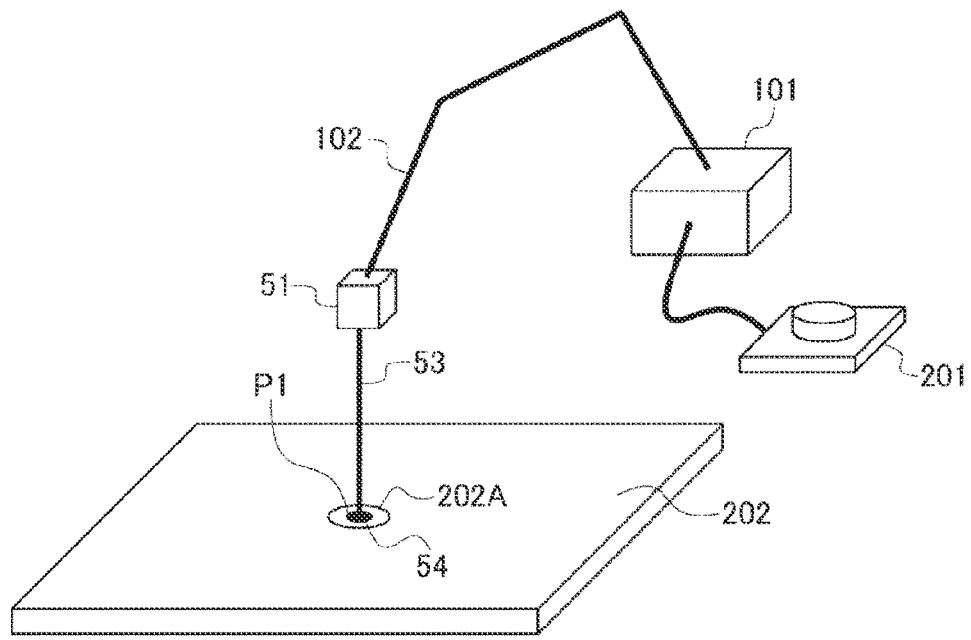
FIG. 7 is a diagram for describing a first method of setting a pivot point.

Here, an example of a pivot point setting method will be described with reference to FIG. 7. FIG. 7 illustrates an example in which the insertion unit 53 is inserted from an insertion port 202A of a skin 202 of the patient and an image of the inside of the living body of the patient is captured.

For example, the user operates the arm portion 102 via the input unit 21 to align the distal end of the insertion unit 53 with the vicinity of the center of the insertion port 202A. In this state, the user presses a button 201 included in the input unit 21. The input unit 21 supplies an input signal indicating that the button 201 has been pressed to the imaging posture control unit 32.

The arm posture control unit 163 detects the posture of the arm portion 102 in a global coordinate system on the basis of the rotation angle of each actuator 171. Here, the global coordinate system is a coordinate system representing an entire three-dimensional space in which the imaging system 11 is present, and is also referred to as a world coordinate system. The arm posture control unit 163 supplies the arm posture data indicating the detected posture of the arm portion 102 to the pivot point setting unit 153.

The pivot point setting unit 153 calculates the position of the distal end of the insertion unit 53 in the global coordinate system on the basis of the posture of the arm portion 102. Then, the pivot point setting unit 153 sets the calculated position of the distal end of the insertion unit 53 as a pivot point P1. As a result, the pivot point P1 is set substantially at the center of the insertion port 202A. The pivot point setting unit 153 supplies data indicating the position of the pivot point P1 in the global coordinate system to the rotation axis setting unit 154 and the target posture setting unit 161.

Thereafter, the user further inserts the insertion unit 53 into the living body by operating the arm portion 102 via the input unit 21.

Figure 6:
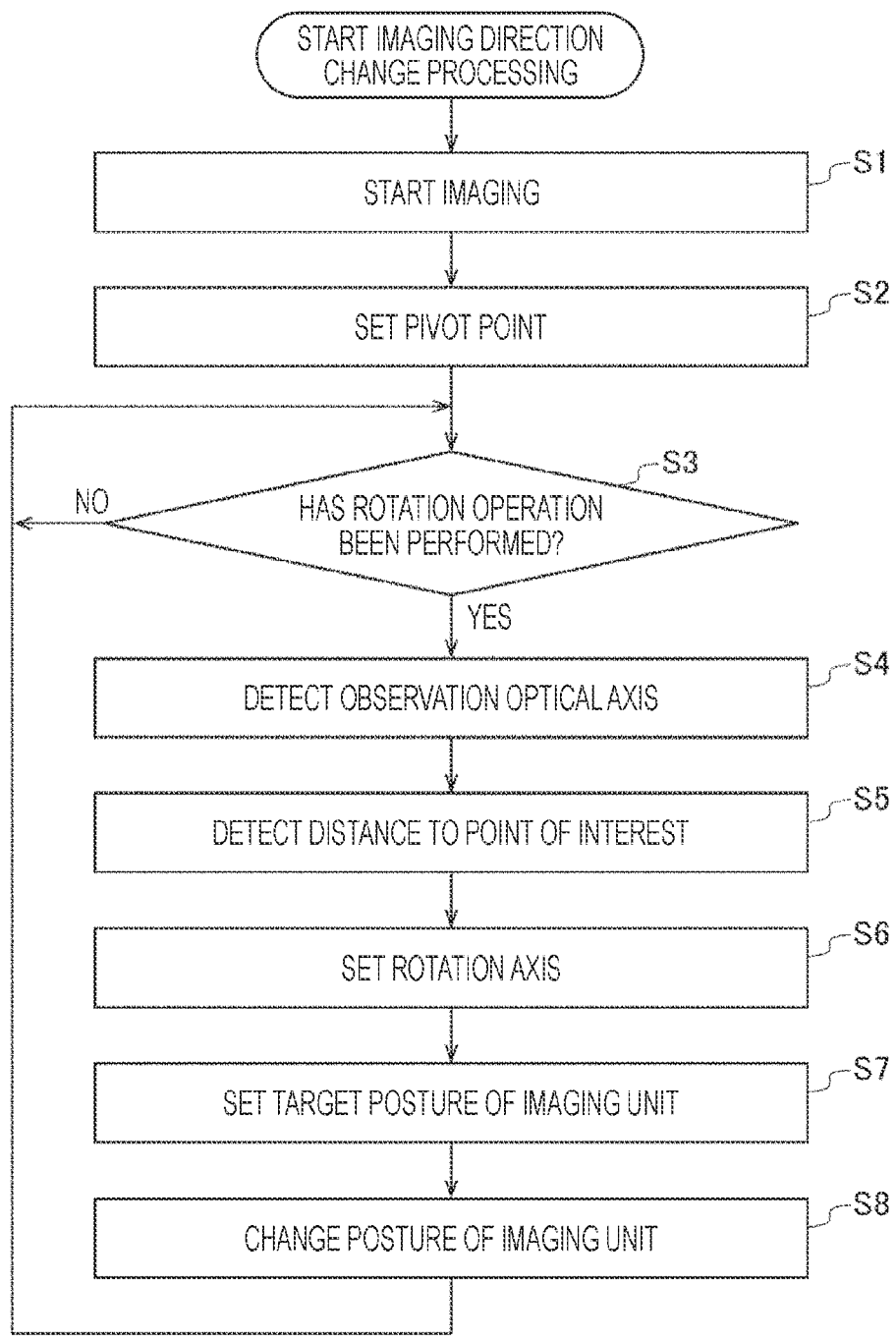
FIG. 6 is a flowchart for describing imaging direction change processing.

For example, as illustrated in FIG. 6, the insertion unit 53 is inserted into the living body from the insertion port 202A. At this time, for example, the insertion unit 53 is inserted into the living body so that the pivot point P1 is positioned on the insertion unit 53. Therefore, the pivot point P1 is a point that is positioned on the insertion unit 53 and not on an observation optical axis A1.

In Step S3, the input unit 21 determines whether or not a rotation operation, that is, an operation of rotating the insertion unit 53 to change the direction in which an image of the subject is captured has been performed. This determination processing is repeated until it is determined that the rotation operation has been performed, and in a case where it is determined that the rotation operation has been performed, the processing proceeds to Step S4.

Note that, as the rotation operation, for example, the user designates an angle and a direction of rotation of the insertion unit 53 around the rotation axis via the input unit 21.

At this time, the angle of rotation of the insertion unit 53 may be expressed by either a relative angle or an absolute angle. In a case where the angle of rotation of the insertion unit 53 is represented by a relative angle, for example, the angle and the direction of rotation of the insertion unit 53 are designated in a form such as an angle of x degrees in a clockwise or counterclockwise direction from the current position. On the other hand, in a case where the angle of rotation of the insertion unit 53 is represented by an absolute angle, for example, the angle of rotation of the insertion unit 53 is designated in a form such as a direction of x degrees based on a predetermined reference position.

In Step S4, the observation optical axis detection unit 152 detects the observation optical axis. Specifically, the input unit 21 supplies an input signal indicating the content of the rotation operation to the imaging control unit 22. The arm posture control unit 163 detects the posture of the arm portion 102 in a global coordinate system on the basis of the rotation angle of each actuator 171. The arm posture control unit 163 supplies the arm posture data indicating the detected posture of the arm portion 102 to the observation optical axis detection unit 152.

The observation optical axis detection unit 152 calculates the posture of the insertion unit 53 in the global coordinate system, in particular, the posture of the observation window 54 on the basis of the posture of the arm portion 102. In addition, the observation optical axis detection unit 152 calculates the posture (position and direction) of the observation optical axis in the global coordinate system on the basis of the posture of the observation window 54. The observation optical axis detection unit 152 supplies data indicating the postures of the observation window 54 and the observation optical axis to the rotation axis setting unit 154 and the target posture setting unit 161.

In Step S5, the distance detection unit 151 detects the distance to the point of interest. For example, the distance detection unit 151 sets, as the point of interest, a point on the subject corresponding to the center of the captured image. As a result, for example, in the example of FIG. 8, an intersection point P2 between the observation optical axis A1 and a surface of a subject 203 is set as the point of interest.

Then, the distance detection unit 151 detects a distance between the observation window 54 and the point of interest on the basis of the left captured image and the right captured image. The distance detection unit 151 supplies data indicating a detection result to the rotation axis setting unit 154. For example, in the example of FIG. 8, a distance between the observation window 54 and the point of interest P2 is detected.

Note that any method can be adopted as a method of detecting the distance between the observation window 54 and the point of interest.

In Step S6, the rotation axis setting unit 154 sets the rotation axis. Specifically, the rotation axis setting unit 154 sets a straight line connecting the pivot point and the point of interest as the rotation axis. For example, in the example of FIG. 8, a straight line connecting the pivot point P1 and the point of interest P2 is set as a rotation axis A2. The rotation axis setting unit 154 supplies data indicating the posture of the rotation axis in the global coordinate system to the target posture setting unit 161.

Figure 8:
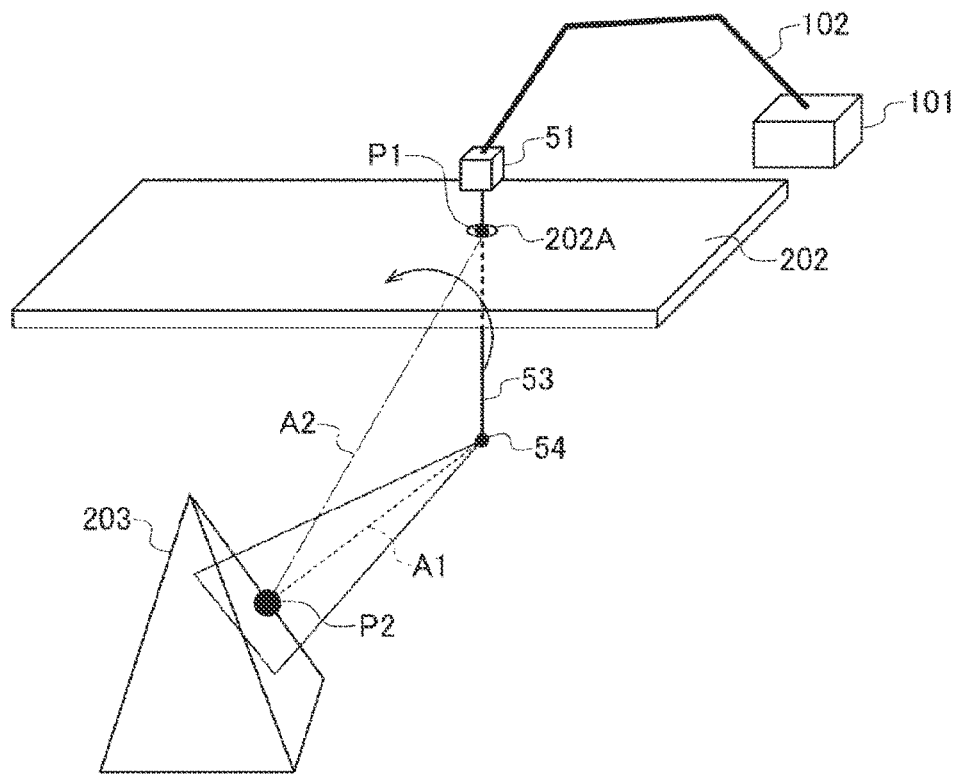
FIG. 8 is a diagram for describing a first method of controlling a posture of the imaging unit.

Here, in the example of FIG. 8, the position of the observation window 54 and the posture of the observation optical axis A1 in the global coordinate system, and the distance between the observation window 54 and the point of interest P2 are known. Therefore, the rotation axis setting unit 154 can calculate the position of the point of interest P2 in the Global coordinate system. Further, the position of the pivot point P1 in the global coordinate system is known. Therefore, the rotation axis setting unit 154 can calculate the posture of the rotation axis A2 connecting the pivot point P1 and the point of interest P2.

In Step S7, the target posture setting unit 161 sets a target posture of the imaging unit 23.

Specifically, the target posture setting unit 161 sets a direction and an amount (rotation angle) of rotation of the insertion unit 53 around the rotation axis on the basis of the content of the rotation operation.

Figure 9:
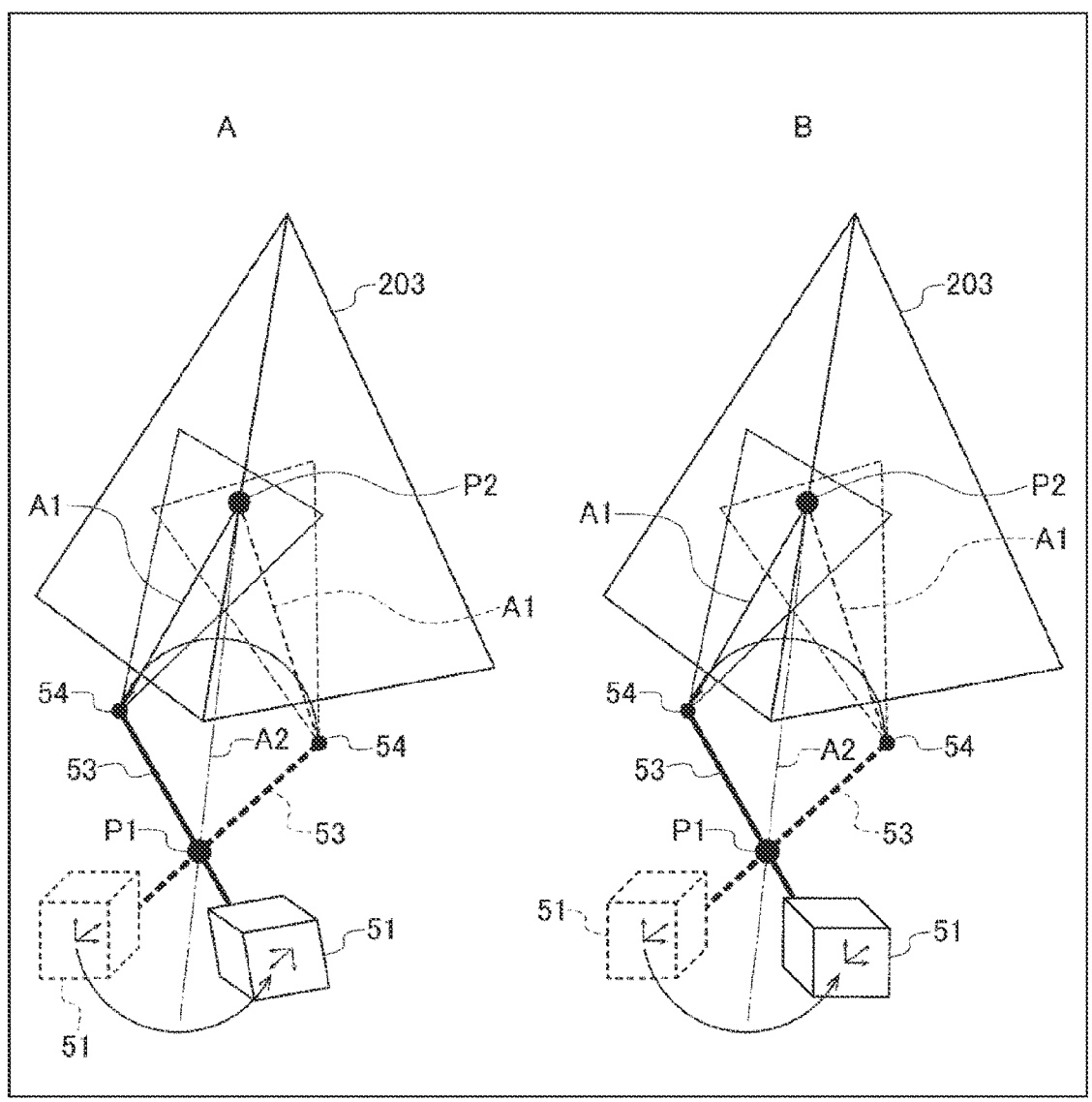
FIG. 9 is a diagram for describing a method of controlling a posture of a camera.

Furthermore, as illustrated in A of FIG. 9, in a case where the insertion unit 53 is rotated around the rotation axis A2, the camera 51 (camera coordinate system) is also rotated. As a result, before and after the rotation of the insertion unit 53, the subject 203 may greatly rotate in the captured image, and visibility may deteriorate.

On the other hand, as illustrated in B of FIG. 9, the target posture setting unit 161 calculates a direction and an amount (rotation angle) of rotation of the camera 51 around the imaging optical axis (z axis) so that directions of the x axis and the y axis of the camera coordinate system in the global coordinate system become substantially the same before and after the rotation of the insertion unit 53. Note that the direction of rotation of the camera 51 around the imaging optical axis is opposite to the direction of rotation of the insertion unit 53 around the rotation axis A2. For example, in a case where the direction of rotation of the insertion unit 53 around the rotation axis A2 is the clockwise correction, the direction of rotation of the camera 51 around the imaging optical axis is the counterclockwise direction.

The target posture setting unit 161 supplies data indicating the direction and the amount of rotation of the insertion unit 53 around the rotation axis to the arm posture control unit 163. In addition, the target posture setting unit 161 supplies data indicating the direction and the amount of rotation of the camera 51 around the imaging optical axis to the camera posture control unit 162.

In Step S8, the posture control unit 155 changes the posture of the imaging unit 23. Specifically, the arm posture control unit 163 drives each actuator 171, moves the arm portion 102, and rotates the insertion unit 53 around the rotation axis in the rotation direction and by the rotation amount, the rotation direction and the rotation amount being set by the target posture setting unit 161. In this case, the observation window 54 is rotated on a circumference around an intersection point between a perpendicular line drawn from the observation window 54 to the rotation axis and the rotation axis.

Figure 10:
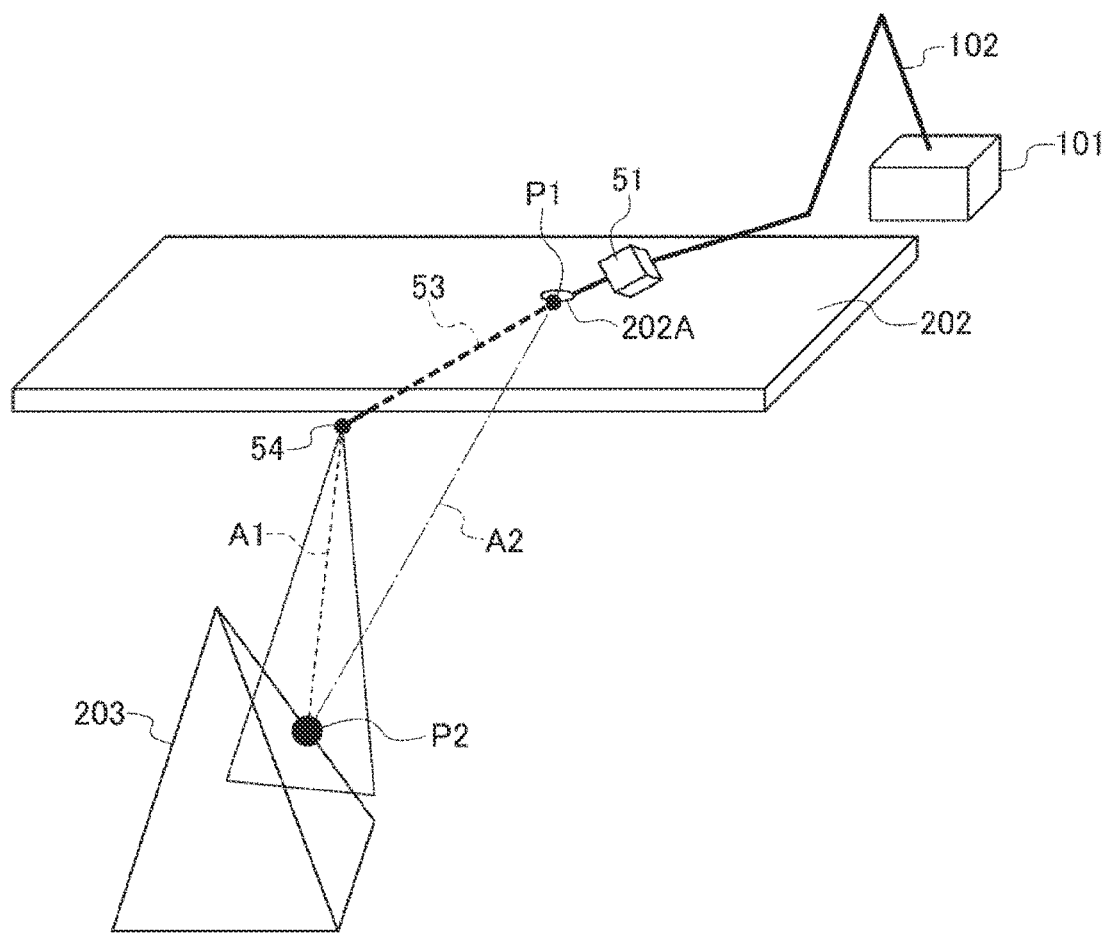
FIG. 10 is a diagram for describing the first method of controlling the posture of the imaging unit.

As a result, for example, the insertion unit 53 is rotated around the rotation axis A2, and is changed from the state illustrated in FIG. 8 to the state illustrated in FIG. 10. Here, since the rotation axis A2 connects the pivot point P1 and the point of interest P2, a state in which the observation optical axis A1 intersects with the subject 203 at the point of interest P2 is maintained while the insertion unit 53 is rotated around the rotation axis A2. Therefore, during and after the rotation of the insertion unit 53, a state in which a point corresponding to the point of interest P2 is positioned substantially at the center in the captured image is maintained.

In addition, the camera posture control unit 162 drives the rotary actuator 52 to rotate the camera 51 around the imaging optical axis in the rotation direction and by the rotation amount, the rotation direction and the rotation amount being set by the target posture setting unit 161. As a result, the camera 51 is rotated around the imaging optical axis so that the rotation of the camera 51 accompanying the rotation of the insertion unit 53 is canceled according to the rotation of the insertion unit 53 around the rotation axis A2. As a result, as illustrated in FIG. 9 described above, even after the insertion unit 53 is rotated, the directions of the a axis and the y axis of the camera coordinate system in the global coordinate system are kept substantially constant. Then, the subject is prevented from greatly rotating around the imaging optical axis in the captured image.

Note that it is desirable that the arm posture control unit 163 and the camera posture control unit 162 are operated in a cooperative manner to make a timing of rotation of the insertion unit 53 and a timing of rotation of the camera 51 be the same as each other, such that the directions of the x axis and the v axis of the camera coordinate system in the global coordinate system are kept substantially constant even during the rotation of the insertion unit 53.

Thereafter, the processing returns to Step S3, and the pieces of processing after Step S3 are performed.

As described above, the direction in which an image of the subject is captured can be easily changed. That is, under a situation where the movement of the insertion unit 53 is limited by the pivot point (insertion port), the user can change the direction in which an image of the subject is captured without finely adjusting the movement of the insertion unit 53. In addition, even in a case where the direction in which an image of the subject is captured is changed, movement of the point of interest in the captured image and vertical inversion of the subject are suppressed. As a result, the user can easily observe the region of interest from different directions without losing sight of the region of interest on the subject.

<Modified Example of Imaging Direction Change Processing>

Next, a modified example of the capturing direction change processing of FIG. 6 will be described with reference to FIGS. 11 to 13.

In Steps S1 to S4, processing similar to the processing described above is performed.

In Step S5, the distance detection unit 151 detects the distance to the point of interest. Here, for example, the user specifies an arbitrary point in the captured image. Then, the distance detection unit 151 detects a distance between the observation window 54 and a point of interest P11 on the subject 203 corresponding to the point specified by the user on the basis of the left captured image and the right captured image. The distance detection unit 151 supplies data indicating a detection result to the rotation axis setting unit 154.

In Step S6, the rotation axis setting unit 154 sets the rotation axis.

Specifically, the rotation axis setting unit 154 calculates the position of the point of interest P11 in the global coordinate system on the basis of the position of the observation window 54 and the posture of the observation optical axis A1 in the global coordinate system, and the distance between the observation window 54 and the point of interest P11. In addition, as illustrated in A of FIG. 11, the rotation axis setting unit 154 calculates the position of an intersection point P12 between a perpendicular line L11 drawn from the point of interest P11 to the observation optical axis and the observation optical axis A1 in the global coordinate system on the basis of the position of the point of interest P11 and the posture of the observation optical axis A1 in the global coordinate system.

Then, the rotation axis setting unit 154 sets a straight line connecting the pivot point P1 and the intersection point P12 as a rotation axis A11, and calculates the posture of the rotation axis A11 in the global coordinate system. The rotation axis setting unit 154 supplies data indicating the posture of the rotation axis A11 in the global coordinate system to the target posture setting unit 161.

In Step S7, the target posture setting unit 161 sets a target posture of the imaging unit 23.

Specifically, the target posture setting unit 161 sets a direction and an amount of rotation of the insertion unit 53 around the rotation axis A11 on the basis of the content of the rotation operation. Further, the target posture setting unit 161 calculates a direction and an amount of rotation of the camera 51 around the imaging optical axis so that directions of the x axis and the y axis of the camera coordinate system in the global coordinate system become substantially the same before and after the rotation of the insertion unit 53. Moreover, the target posture setting unit 161 sets a target position of the point of interest P11 in the captured image after the rotation of the insertion unit 53 and the camera 51. The target position of the point of interest P11 may be set by the user, or may be automatically set by the target posture setting unit 161, for example. Then, the target posture setting unit 161 calculates a direction and an amount (rotation angle) of rotation of the insertion unit 53 around the pivot point P1 so that the point of interest P11 is moved to the target position in the captured image after the rotation of the insertion unit 53 and the camera 51.

The target posture setting unit 161 supplies, to the arm posture control unit 163, data indicating the direction and the amount of rotation of the insertion unit 53 around the rotation axis A11 and the direction and the amount of rotation of the insertion unit 53 around the pivot point P1. In addition, the target posture setting unit 161 supplies data indicating the direction and the amount of rotation of the insertion unit 53 around the imaging optical axis to the camera posture control unit 162.

In Step S8, the posture control unit 155 changes the posture of the imaging unit 23. Specifically, the arm posture control unit 163 drives each actuator 171, moves the arm portion 102, and rotates the insertion unit 53 around the rotation axis A11 in the rotation direction and by the rotation amount as illustrated in B of FIG. 11, the rotation direction and the rotation amount being set by the target posture setting unit 161. In addition, the camera posture control unit 162 drives the rotary actuator 52 to rotate the camera 51 around the imaging optical axis in the rotation direction and by the rotation amount, the rotation direction and the rotation amount being set by the target posture setting unit 161. Note that, as described above, it is desirable that the arm posture control unit 163 and the camera posture control unit 162 are operated in a cooperative manner to make a timing of rotation of the insertion unit 53 and a timing of rotation of the camera 51 be the same as each other.

Figure 11:
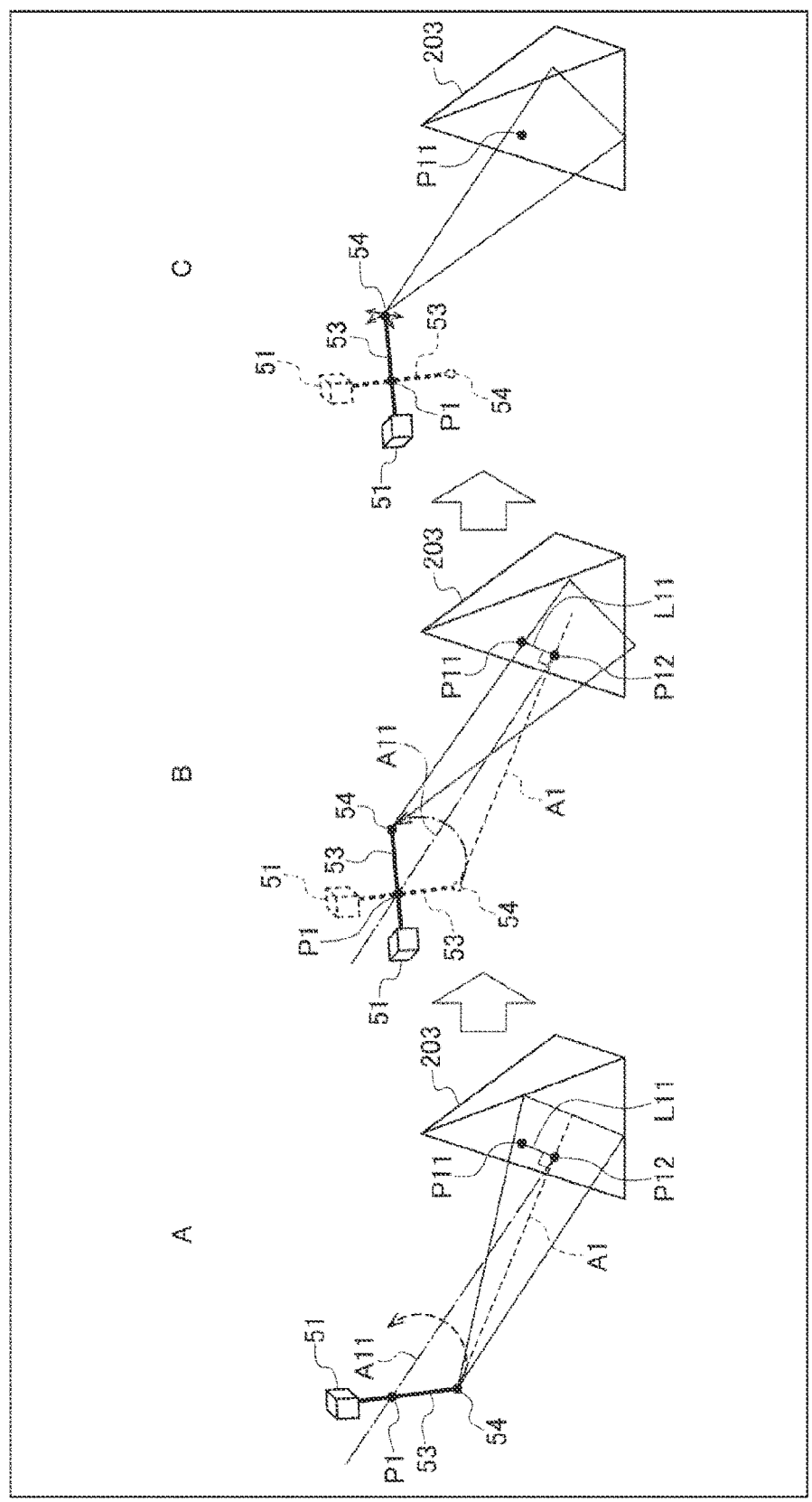
FIG. 11 is a diagram for describing a second method of controlling the posture of the imaging unit.

Next, the arm posture control unit 163 drives each actuator 171, moves the arm portion 102, and rotates the insertion unit 53 around the pivot point P1 in the rotation direction and by the rotation amount as illustrated in C of FIG. 11, the rotation direction and the rotation amount being set by the target posture setting unit 161. In this case, the observation window 54 is rotated on a circumference around the pivot point P1. As a result, the point of interest P11 reaches the target position in the captured image.

Thereafter, the processing returns to Step S3, and the pieces of processing after Step S3 are performed.

As described above, the rotation of the insertion unit 53 around the rotation axis A11 and the rotation of the insertion unit 53 around the pivot point P1 are controlled, whereby the position of the point of interest P11 in the captured image is controlled.

For example, in a case where the target position of the point of interest P11 in the captured image is set to the same position as that before the rotation, the direction in which an image of the subject 203 is captured can be changed without substantially moving the point of interest P11 on the subject 203 in the captured image.

Figure 12:
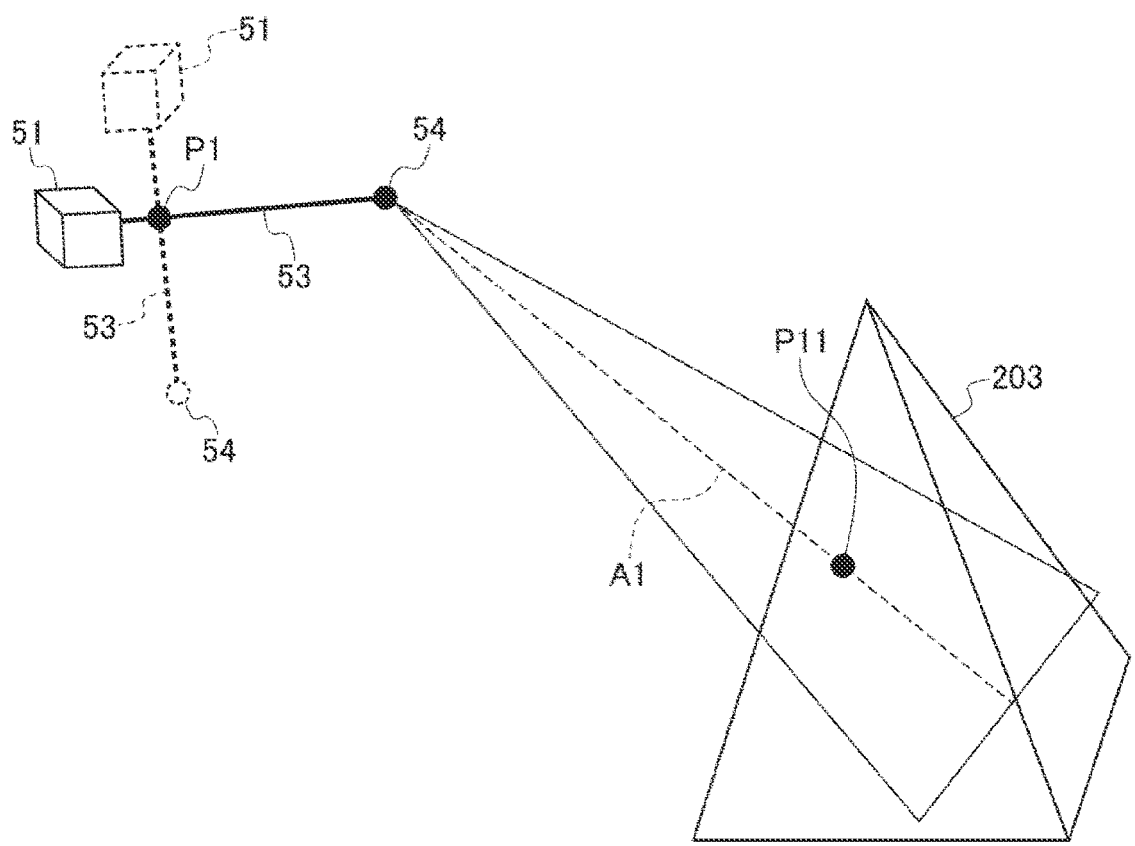
FIG. 12 is a diagram for describing the second method of controlling the posture of the imaging unit.

Furthermore, for example, in a case where the target position of the point of interest P11 in the captured image is set at the center of the captured image, the posture of the insertion unit 53 is adjusted so that the observation optical axis A1 passes through the point of interest P11 as illustrated in FIG. 12. As a result, the point of interest P11 on the subject 203 can be moved to the center of the captured image while charging the direction in which an image of the subject 203 is captured.

Note that, for example, by rotating the insertion unit 53 around the pivot point P1 in parallel with the rotation of the insertion unit 53 around the rotation axis A11, the point of interest P11 may be moved to the target position in the captured image in parallel with the change of the direction in which an image of the subject is captured.

Figure 13:
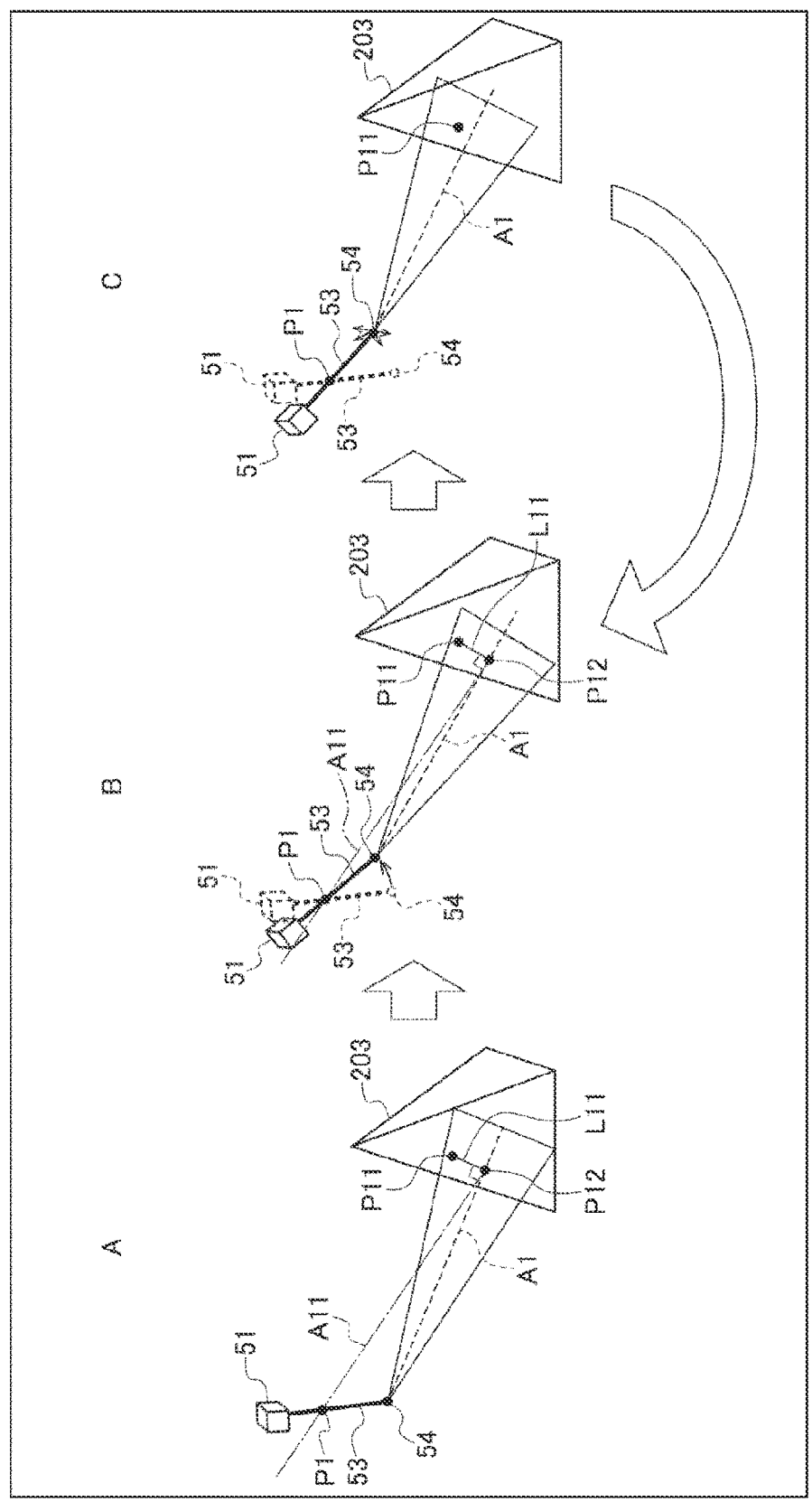
FIG. 13 is a diagram for describing a third method of controlling the posture of the imaging unit.

For example, A of FIG. 13 illustrates the same state as A of FIG. 11.

Next, as illustrated in B of FIG. 13, the insertion unit 53 is rotated around the rotation axis A11 by a predetermined amount. At this time, the camera 51 is rotated around the imaging optical axis in accordance with the rotation of the insertion unit 53 around the rotation axis A11.

Next, as illustrated in C of FIG. 13, the insertion unit 53 is rotated by a predetermined amount around the pivot point P1 so that the position of the point of interest P11 in the captured image approaches the target position. Note that, in a case where the target position of the point of interest P11 is set to the same position as that before the rotation, the insertion unit 53 is rotated around the pivot point P1 so that the position of the point of interest P11 in the captured image is moved to the target position.

Then, by alternately repeating the processing in B of FIG. 13 and the processing in C of FIG. 13, the point of interest P11 moved to the target position in the captured image substantially at the same time as the rotation of the insertion unit 53 around the rotation axis A11 ends.

Note that the processing in B of FIG. 13 and the processing in C of FIG. 13 are performed in synchronization with a frame interval of the camera 51. For example, every time the processing in B of FIG. 13 and the processing in C of FIG. 13 end, the captured image is obtained.

As a result, for example, in a case where the target position of the point of interest P11 is the same as that before the rotation, the point of interest P11 is fixed at substantially the same position in the captured image during and after the rotation of the insertion unit 53. On the other hand, in a case where the target position of the point of interest P11 is different from that before the rotation, the point of interest P11 is gradually brought close to the target position in the captured image. Therefore, for example, the user is prevented from losing sight of the region of interest around the point of interest P11.

Note that, in C of FIG. 13, as the insertion unit 53 is rotated around the pivot point P1, the intersection point between the perpendicular line drawn from the point of interest P11 to the observation optical axis A1 and the observation optical axis is moved. Therefore, for example, it is desirable to change, after the processing in C of FIG. 13 and before the processing in B of FIG. 13, the rotation axis A11 so as to connect the pivot point P1 and the intersection point after the movement.

As described above, the user can easily change the direction in which an image of the subject is captured, set an arbitrary point on the subject as the point of interest, and move the point of interest to an arbitrary target position in the captured image.

2. Modified Examples

Hereinafter, modified examples of the above-described embodiment of the present technology will be described.
<Modified Examples Related to Pivot Point Setting Method>

Figure 14:
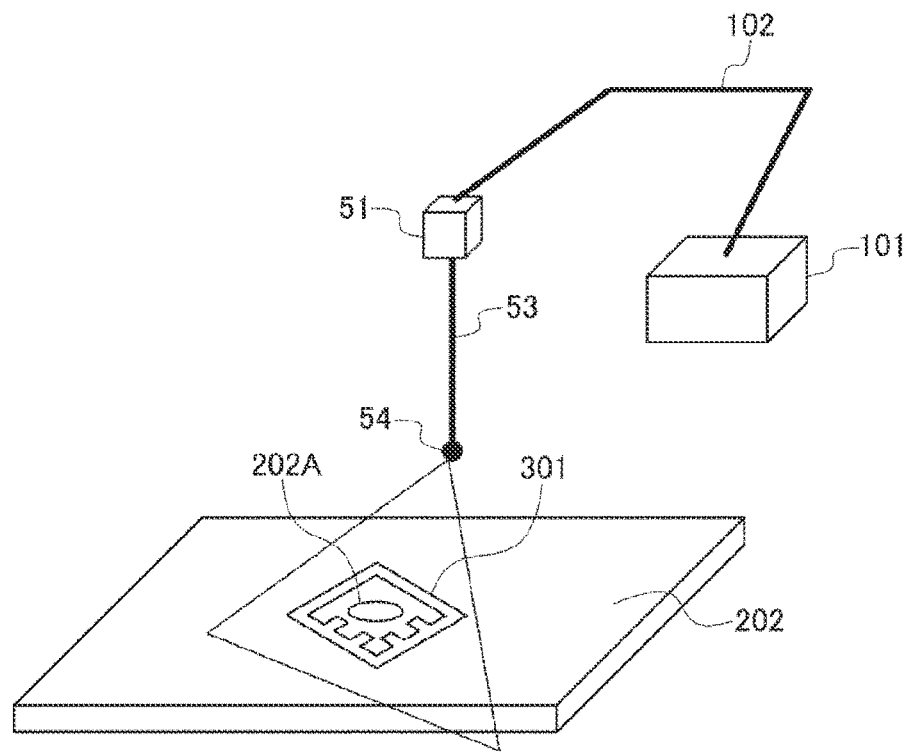
FIG. 14 is a diagram for describing a second method of setting the pivot point.

For example, as illustrated in FIG. 14, a marker 301 is provided around the insertion port 202A of the skin 202 of the patient, and the camera 51 captures an image of the periphery of the marker 301 before the insertion of the insertion unit 53. Note that the marker 301 is implemented by an arbitrary method such as bonding, printing, or irradiation with pattern light. Then, a distance between the observation window 54 and the center of the insertion port 202A in the marker 301 is detected on the basis of the left captured image and the right captured image. Furthermore, the position of the observation window 54 in the global coordinate system is detected on the basis of the posture of the arm portion 102. Then, the position of the center of the insertion port 202A in the global coordinate system is detected on the basis of the position of the observation window 54 in the global coordinate system and the distance between the observation window 54 and the center of the insertion port 202A in the marker 301. Then, the position of the center of the insertion port 202A in the global coordinate system is set as the pivot point.

Figure 15:
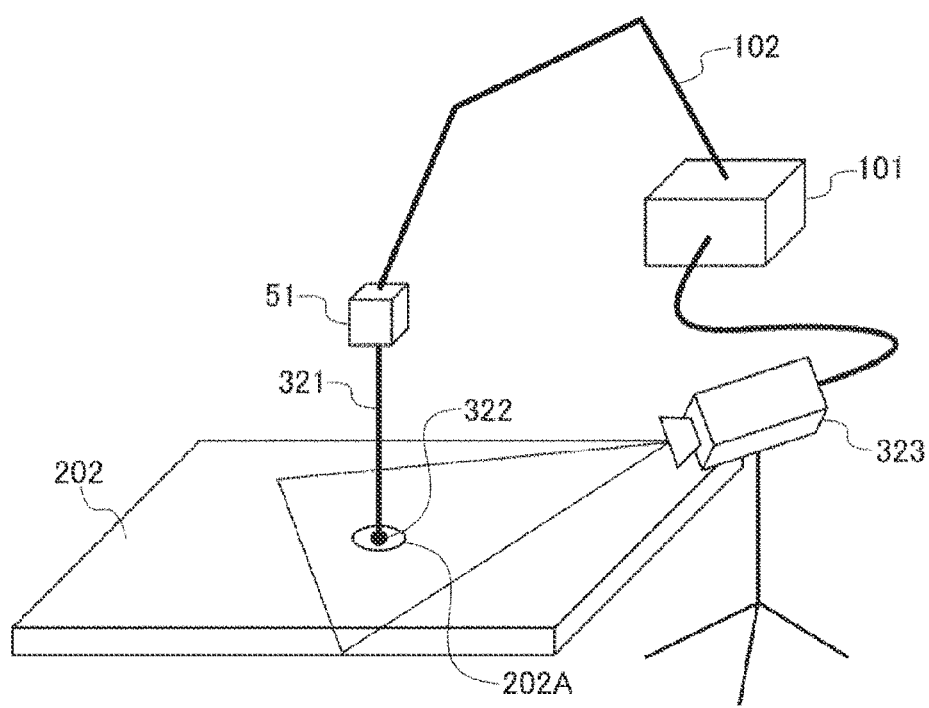
FIG. 15 is a diagram for describing a third method of setting the pivot point.

Furthermore, for example, as illustrated in FIG. 15, an insertion unit 321 is provided instead of the insertion unit 53 of the imaging unit 23. An observation window 322 is provided on a distal end surface of the insertion unit 321 similarly to the insertion unit 53. Furthermore, a marker (not illustrated) having a predetermined pattern is provided at a distal end of the insertion unit 321. Moreover, a camera 323 captures an image of the periphery of the insertion port 202A, and supplies the obtained captured image to the pivot point setting unit 153 in the base portion 101.

In a process of inserting the insertion unit 321 into the living body from the insertion port 202A, the pivot point setting unit 153 detects a moment at which the distal end of the insertion unit 321 enters the insertion port 202A and the marker at the distal end of the insertion unit 321 becomes invisible in the captured image from the camera 323. The pivot point setting unit 153 calculates the position of the distal end of the insertion unit 321 in the global coordinate system on the basis of the posture of the arm portion 102 at the time of obtaining the captured image at the moment at which the marker at the distal end of the insertion unit 321 becomes invisible. Then, the pivot point setting unit 153 sets the calculated position of the distal end of the insertion unit 321 as the pivot point.

Note that, for example, a light emitting element may be provided at the distal end of the insertion unit 321 instead of the marker, and the pivot point setting unit 153 may detect a moment at which the light emitting element becomes invisible in the captured image from the camera 51.

Furthermore, for example, in a case where the pivot point is fixed, for example, in a case where imaging is performed by inserting the insertion unit from a predetermined insertion port of a fixed machine, the pivot point setting processing may be omitted.

Moreover, for example, in a case where there is a possibility that the pivot point is moved, for example, in the processing in FIG. 6, the pivot point setting processing may be performed every time the rotation operation is performed.
<Processing in Case of Moving Point of Interest>

For example, as illustrated in A of FIG. 16, a case where the point of interest is moved from a point P21 on a subject 352 to a point P22 on a subject 353 by rotating the insertion unit 53 around the pivot point P1 will be described.

In this case, in a case where the insertion unit 53 is rotated around the pivot point P1 as it is, the angle of the observation optical axis A1 with respect to a normal vector at the point P22 of the subject 353 is increased. That is, an image of the periphery of the point P22 is captured in a direction greatly inclined obliquely from the front. Therefore, the visibility of the periphery of the point P22 in the captured image may deteriorate.

On the other hand, in a case where the insertion unit 53 is rotated around the pivot point P1, the insertion unit 53 may be rotated after the observation window 54 (observation optical axis) is oriented in a direction in which the observation window 54 (insertion unit 53) is rotated.

Figure 16:
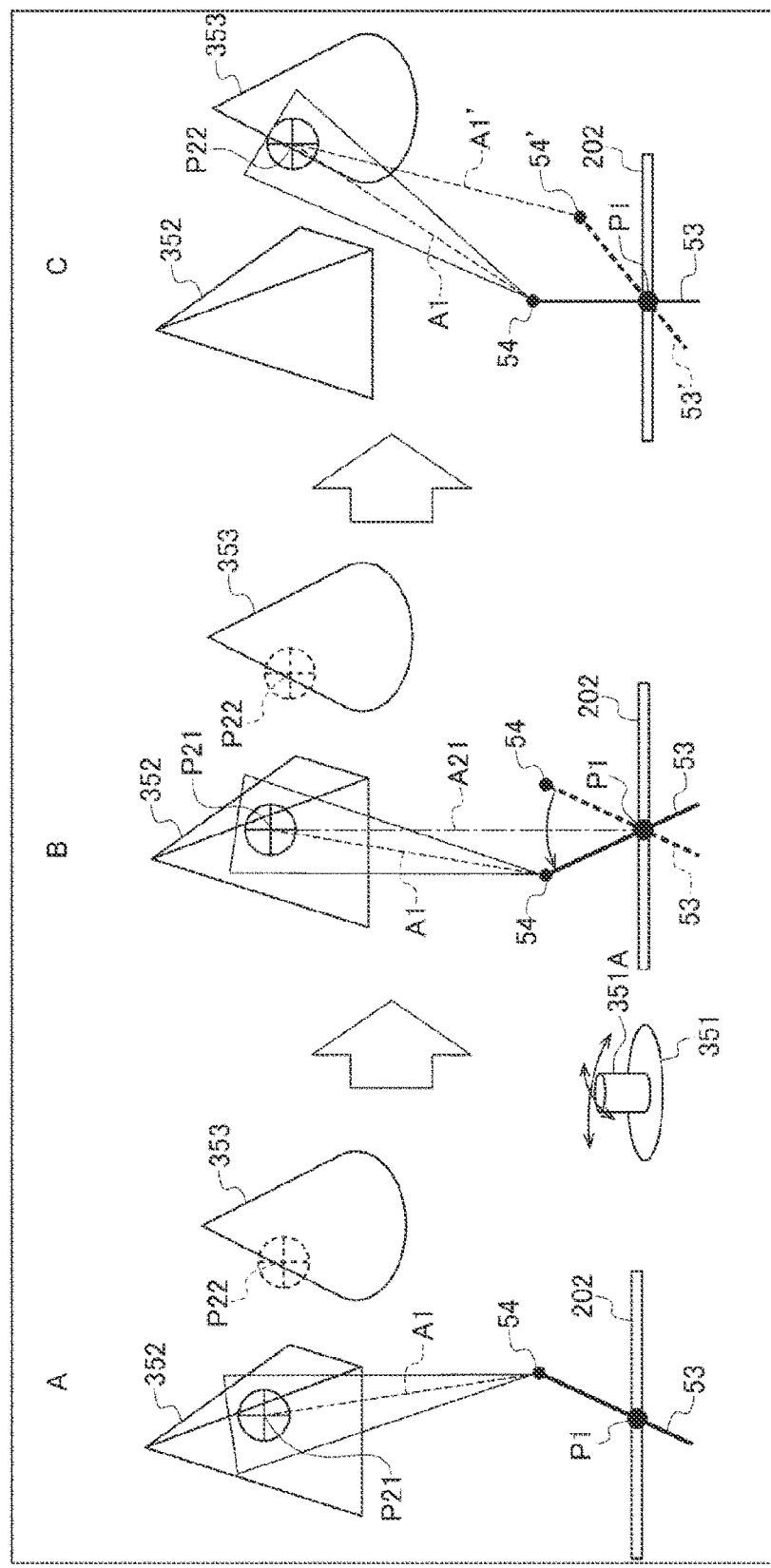
FIG. 16 is a diagram for describing a fourth method of controlling the posture of the imaging unit.

Specifically, for example, first, as illustrated in B of FIG. 16, the insertion unit 53 is rotated around a rotation axis A21 connecting the pivot point P1 and a point P21 so that the orientation of the observation window 54 (the orientation of the observation optical axis A1) approaches the direction of rotation of the observation window 54 (the insertion unit 53) around the pivot point P1.

Then, as illustrated in C of FIG. 16, the insertion unit 53 is rotated around the pivot point P1 so that the observation optical axis A1 intersects with the point P22 on the subject 353.

Note that an insertion unit 53', an observation window 54', and an observation optical axis A1' in C of FIG. 16 indicate the positions of the insertion unit 53, the observation window 54, and the observation optical axis A1 in a case where the insertion unit 53 is rotated around the pivot point P1 without being rotated around the rotation axis A21. The observation optical axis A1 has a smaller angle with respect to the normal vector at the point P22 of the subject 353 than the observation optical axis A1'. That is, by rotating the insertion unit 53 around the rotation axis A21, an image of the periphery of the point P22 can be captured in a direction closer to the front, and the visibility is improved.

Note that the processing of orienting the observation window 54 (observation optical axis A1) in the rotation direction of the observation window 54 may be automatically performed or may be performed by a user operation.

In the latter case, for example, in a case where a stick 351A of a stick controller 351 included in the input unit 21 is tilted by a predetermined angle or more, or is continuously tilted in the same direction for a predetermined time or more, processing of orienting the observation window 54 in the rotation direction of the observation window 54 may be performed.

Furthermore, in both a case where the orientation processing is automatically performed and a case where the orientation processing is performed by a user operation, on/off of a function of orienting the observation window 54 in the rotation direction of the observation window 54 may be switched.

Moreover, similarly to the example of FIG. 13 described above, the rotation of the insertion unit 53 around the pivot point P1 and the rotation of the insertion unit 53 around the rotation axis A21 may be alternately repeated little by little.

<Modified Example Related to Method of Detecting Distance to Point of Interest>

In the above description, an example in which the distance between the observation window 54 and the point of interest is detected using a stereo camera system has been described, but other detection methods may be used.

For example, the distance to the point of interest may be detected using a laser, an ultrasonic sensor, an infrared sensor, a depth sensor, or the like.

Furthermore, a distance to each point around the point of interest may also be detected according to the degree of unevenness of the surface of the subject, and an average value of the detected distances or the like may be used as the distance to the point of interest.

Furthermore, for example, in a case where a positional relationship between the insertion unit 53 and the subject and a three-dimensional shape of the subject are known in advance, the processing of detecting the distance to the point of interest may be omitted. Such a case is assumed to be, for example, a case where a three-dimensional shape of the inside of the body of the patient is known by a computed tomography (CT) scan or the like.

<Modified Example Related to Arm Portion>

In the above description, an example in which the posture of the arm portion 102 is detected on the basis of the rotation angle of each actuator 171 has been described, but other detection directions may be used.

For example, a marker may be provided on each part of the arm portion 102, the position of each marker may be detected by a motion capture system or the like, and the posture of the arm portion 102 may be detected on the basis of the position of each marker.

Furthermore, the configuration of the arm portion is not limited to the above-described configuration, and can be arbitrarily changed. For example, it is possible to increase the number of joints or change the direction or angle in or at which the joints are bent.

<Modified Example Related to Insertion Unit>

In the above description, an example in which the insertion unit is implemented by a rigid endoscope has been described, but the present technology can also be applied to a case where the insertion unit is implemented by a flexible endoscope such as a fiberscope, for example.

Furthermore, for example, the imaging unit may be provided at the distal end of the insertion unit. That is, the imaging unit may be provided so that the optical axis (imaging optical axis=observation optical axis) is inclined with respect to the central axis of the insertion unit.

<Example of Application of Present Technology>

The present technology can be generally applied to a case of capturing an image by rotating a rod-shaped optical member whose observation optical axis is inclined with respect to a central axis around a pivot point as a fulcrum, in addition to the case of capturing an image of the inside of a living body described above.

3. Others

<Example of Configuration of Computer>

The series of pieces of processing described above can be performed by hardware or can be executed by software. In a case where the series of pieces of processing is performed by software, a program constituting the software is installed in a computer. Here, the computer includes a computer incorporated in dedicated hardware, a general-purpose personal computer capable of executing various functions by installing various programs, and the like, for example.

Figure 17:
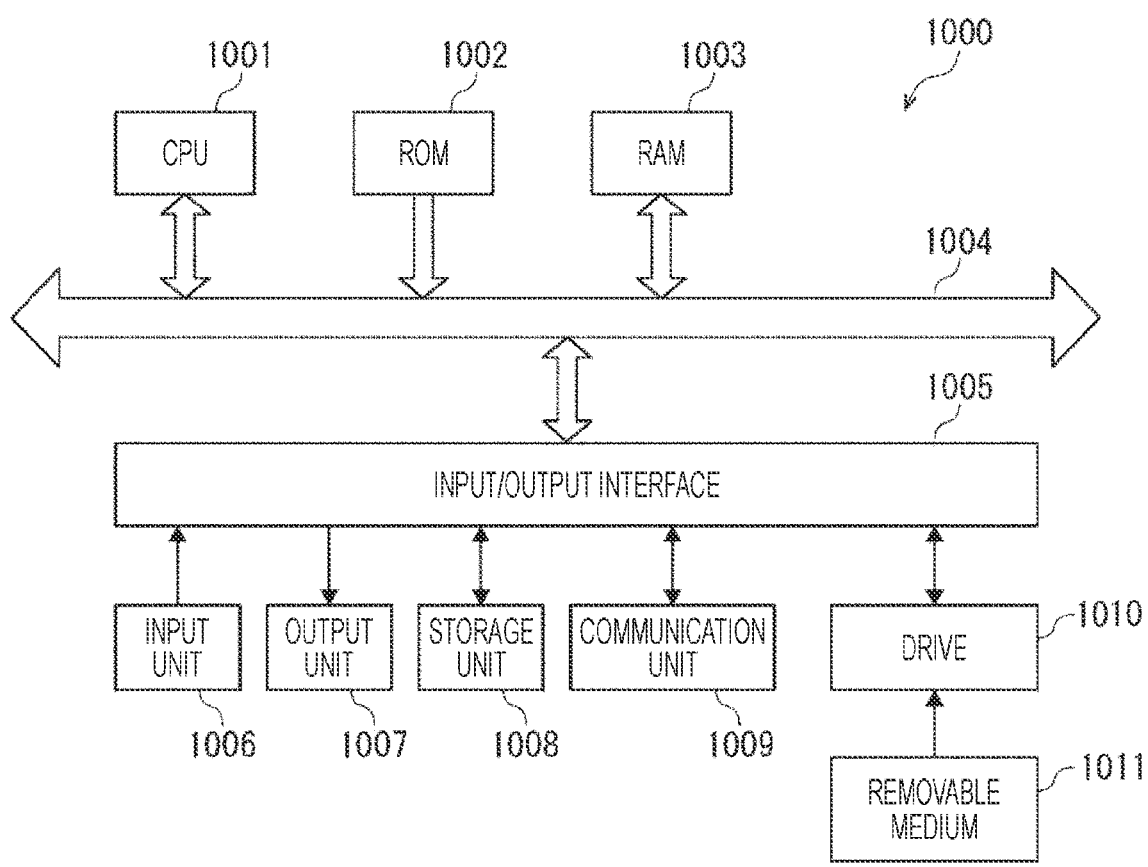
FIG. 17 is a block diagram illustrating an example of a configuration of a computer.

FIG. 17 is a block diagram illustrating an example of a configuration of hardware of a computer 1000 performing the series of pieces of processing described above by using a program.

In the computer 1000, a central processing unit (CPU) 1001, a read only memory (ROM) 1002, and a random access memory (RAM) 1003 are connected to one another by a bus 1004.

Moreover, an input/output interface 1005 is connected to the bus 1004. An input unit 1006, an output unit 1007, a storage unit 1008, a communication unit 1009, and a drive 1010 are connected to the input/output interface 1005.

The input unit 1006 includes a keyboard, a mouse, a microphone, and the like. The output unit 1007 includes a display, a speaker, and the like. The storage unit 1008 includes a hard disk, a nonvolatile memory, and the like. The communication unit 1009 includes a network interface and the like. The drive 1010 drives a removable medium 1011 such as a magnetic disk, an optical disk, a magneto-optical disk, or a semiconductor memory.

In the computer 1000 configured as described above, the CPU 1001 loads, for example, a program stored in the storage unit 1008 to the RAM 1003 through the input/output interface 1005 and the bus 1004, and executes the program, such that the series of pieces of processing described above is performed.

The program executed by the computer 1000 (CPU 1001) can be provided by being recorded in the removable medium 1011 as a package medium or the like, for example. Furthermore, the program can be provided via a wired or wireless transmission medium such as a local area network, the Internet, or digital satellite broadcasting.

In the computer 1000, the program can be installed in the storage unit 1008 via the input/output interface 1005 by mounting the removable medium 1011 on the drive 1010. Furthermore, the program can be received by the communication unit 1009 via a wired or wireless transmission medium and installed in the storage unit 1008. In addition, the program can be installed in the ROM 1002 or the storage unit 1008 in advance.

Note that the program executed by the computer 1000 may be a program by which the pieces of processing are performed in time series in the order described in the present specification, or may be a program by which the pieces of processing are performed in parallel or at a necessary timing such as when a call as performed or the like.

In addition, in the present specification, a system means a set of a plurality of components (devices, modules (parts), or the like), and it does not matter whether or not all the components are in the same housing. Therefore, a plurality of devices housed in separate housings and connected via a network and one device in which a plurality of modules is housed in one housing are both systems.

Note that the embodiment of the present technology is not limited to that described above, and may be variously changed without departing from the gist of the present technology.

For example, the present technology can have a configuration of cloud computing in which one function is performed in cooperation by a plurality of devices via a network.

Furthermore, each step described in the above-described flowchart can be performed by one device or can be performed in a distributed manner by a plurality of devices.

Moreover, in a case where a plurality of pieces of processing is included in one step, the plurality of pieces of processing included in the one step can be performed by one device or can be performed in a distributed manner by a plurality of devices.

<Example of Combination of Configurations>

Note that the present technology can also have the following configuration.

(1)

An imaging control device including:

a rotation axis setting unit that sets a rotation axis on the basis of a pivot point and a point of interest on a subject, the pivot point serving as a fulcrum of a rod-shaped optical member whose observation optical axis is inclined with respect to a central axis and being not positioned on the observation optical axis; and a posture control unit that rotates the optical member around the rotation axis.

(2)

The imaging control device according to (1), in which an imaging device that captures an image of the subject via the optical member is connected to the optical member so as to be rotatable around an optical axis of the imaging device, and the posture control unit rotates the imaging device around the optical axis of the imaging device in a second direction opposite to a first direction according to rotation of the optical member around the rotation axis in the first direction.

(3)

The imaging control device according to (1) or (2), in which the rotation axis setting unit sets a straight line connecting the pivot point and the point of interest as the rotation axis.

(4)

The imaging control device according to (3), in which the point of interest includes a point on the subject corresponding to the center of a captured image obtained by capturing the image of the subject via the optical member.

(5)

The imaging control device according to (1) or (2), in which the posture control unit controls the rotation of the optical member around the rotation axis and the rotation of the optical member around the pivot point to control the position of the point of interest in a captured image obtained by capturing the image of the subject via the optical member.

(6)

The imaging control device according to (5), in which the posture control unit controls the rotation of the optical member around the pivot point so that the point of interest in the captured image after the rotation of the optical member around the rotation axis reaches a target position.

(7)

The imaging control device according to (6), in in which the target position is set at the position of the point of interest in the captured image before the rotation of the optical member around the rotation axis or at the center of the captured image.

(8)

The imaging control device according to (6) or (7), in which the posture control unit causes the rotation of the optical member around the rotation axis and the rotation of the optical member around the pivot point to be alternately repeated until the point of interest in the captured image reaches the target position as the optical member is rotated around the rotation axis by a predetermined rotation amount.

(9)

The imaging control device according to any one of (5) to (8), in which the point of interest includes a point on the subject corresponding to a point specified in the captured image.

(10)

The imaging control device according to any one of (5) to (9), in which
the rotation axis setting unit sets, as the rotation axis, a straight line connecting an intersection point between a perpendicular line drawn from the point of interest to the observation optical axis and the observation optical axis, and the pivot point.

(11)

The imaging control device according to any one of (1) to (10), in which
the optical member is inserted into a living body, and
the pivot point includes a point on the optical member in the vicinity of an insertion port through which the optical member is inserted into the living body.

(12)

The imaging control device according to (11), further including
a pivot point setting unit that sets, as the pivot point, a point on the optical member in the vicinity of the insertion port.

(13)

The imaging control device according to (11) or (12), in which
the optical member includes a rigid endoscope or a flexible endoscope.

(14)

The imaging control device according to any one of (1) to (13), in which
in a case of rotating the optical member around the pivot point is the first direction, the posture control unit rotates the optical member around the rotation axis in the second direction to bring a direction of the observation optical axis close to the first direction.

(15)

The imaging control device according to any one of (1) to (14), further including
an observation optical axis detection unit that detects the observation optical axis on the basis of a posture of the optical member.

(16)

The imaging control device according to any one of (1) to (15), in which
the posture control unit controls the rotation of the optical member by controlling a posture of an arm portion that moves the optical member.

(17)

An imaging control method including:
setting a rotation axis on the basis of a pivot point and a point of interest on a subject, the pivot point serving as a fulcrum of a rod-shaped optical member whose observation optical axis is inclined with respect to a central axis and being not positioned on the observation optical axis; and
rotating the optical member around the rotation axis.

(18)

A program for causing a computer to execute processing of:
setting a rotation axis on the basis of a pivot point and a point of interest on a subject, the pivot point serving as a fulcrum of a rod-shaped optical member whose observation optical axis is inclined with respect to a central axis and being not positioned on the observation optical axis; and
rotating the optical member around the rotation axis.

(19)

An imaging system including:
an imaging unit that includes a rod-shaped optical member whose observation optical axis is inclined with respect to a central axis;
a rotation axis setting unit that sets a rotation axis on the basis of a pivot point and a point of interest on a subject, the pivot point serving as a fulcrum of the optical member and being not positioned on the observation optical axis; and
a posture control unit that rotates the optical member around the rotation axis.

Note that the effects described in the present specification are merely illustrative and not limitative, and the present technology may have other effects.

REFERENCE SIGNS LIST

11 Imaging system
22 Imaging control unit
23 Imaging unit
26 Arm mechanism
51 Camera
52 Rotary actuator
53 Insertion unit
54a, 54b Observation window
102 Arm portion
112-1 to 112-4 Joint portion
151 Distance detection unit
152 Observation optical axis detection unit
153 Pivot point setting unit
154 Rotation axis setting unit
155 Posture control unit
161 Target posture setting unit
162 Camera posture control unit
163 Arm posture control unit
171-1 to 171-n Actuator

The invention claimed is:

1. An imaging control device comprising:
a rotation axis setting unit configured to set a rotation axis on a basis of a pivot point and a point of interest on a subject, the pivot point serving as a fulcrum of a rod-shaped optical member whose observation optical axis is inclined with respect to a central axis, wherein the pivot point is not positioned on the observation optical axis;
a pivot point setting unit configured to set a point on the optical member as the pivot point; and
a posture control unit configured to
rotate the optical member around the rotation axis, and
rotate the optical member around the pivot point,
wherein the point on the optical member is set as the pivot point according to performance of a rotation operation by a user, and
wherein the rotation axis setting unit, the pivot point setting unit, and the posture control unit are each implemented via at least one processor.

2. The imaging control device according to claim 1, wherein
an imaging device configured to capture an image of the subject via the optical member is connected to the optical member so as to be rotatable around an optical axis of the imaging device, and
the posture control unit is further configured to rotate the imaging device around the optical axis of the imaging device in a second direction opposite to a first direction according to rotation of the optical member around the rotation axis in the first direction.

3. The imaging control device according to claim 1, wherein
in a case of rotating the optical member around the pivot point in a first direction, the posture control unit rotates the optical member around the rotation axis in a second direction to bring a direction of the observation optical axis close to the first direction.

4. The imaging control device according to claim 1, further comprising
an observation optical axis detection unit that detects the observation optical axis on a basis of a posture of the optical member.

5. The imaging control device according to claim 1, wherein
the posture control unit controls the rotation of the optical member by controlling a posture of an arm portion that moves the optical member.

6. The imaging control device according to claim 1, wherein
the pivot point setting unit sets the point on the optical member as the pivot point based on visibility of a distal end of the optical member.

7. The imaging control device according to claim 1, wherein
the rotation axis setting unit sets a straight line connecting the pivot point and the point of interest as the rotation axis.

8. The imaging control device according to claim 7, wherein
the point of interest includes a point on the subject corresponding to a center of a captured image obtained by capturing an image of the subject via the optical member.

9. The imaging control device according to claim 1, wherein
the optical member is configured to be inserted into a living body, and
the pivot point includes the point on the optical member in a vicinity of an insertion port through which the optical member is inserted into the living body.

10. The imaging control device according to claim 9, wherein the pivot point setting unit sets, as the pivot point, the point on the optical member in the vicinity of the insertion port.

11. The imaging control device according to claim 9, wherein
the optical member includes a rigid endoscope or a flexible endoscope.

12. The imaging control device according to claim 1, wherein
the posture control unit controls the rotation of the optical member around the rotation axis and the rotation of the optical member around the pivot point to control a position of the point of interest in a captured image obtained by capturing an image of the subject via the optical member.

13. The imaging control device according to claim 12, wherein
the point of interest includes a point on the subject corresponding to a point specified in the captured image.

14. The imaging control device according to claim 12, wherein
the rotation axis setting unit sets, as the rotation axis, a straight line connecting an intersection point between a perpendicular line drawn from the point of interest to the observation optical axis and the observation optical axis, and the pivot point.

15. The imaging control device according to claim 12, wherein
the posture control unit controls the rotation of the optical member around the pivot point so that the point of interest in the captured image after the rotation of the optical member around the rotation axis reaches a target position.

16. The imaging control device according to claim 15, wherein
the target position is set at the position of the point of interest in the captured image before the rotation of the optical member around the rotation axis or at a center of the captured image.

17. The imaging control device according to claim 15, wherein
the posture control unit causes the rotation of the optical member around the rotation axis and the rotation of the optical member around the pivot point to be alternately repeated until the point of interest in the captured image reaches the target position as the optical member is rotated around the rotation axis by a predetermined rotation amount.

18. An imaging control method performed by an imaging control device, the imaging control method comprising:
setting a rotation axis on a basis of a pivot point and a point of interest on a subject, the pivot point serving as a fulcrum of a rod-shaped optical member whose observation optical axis is inclined with respect to a central axis and being not positioned on the observation optical axis;
setting a point on the optical member as the pivot point;
rotating the optical member around the rotation axis; and
rotating the optical member around the pivot point,
wherein the point on the optical member is set as the pivot point according to performance of a rotation operation by a user.

19. A non-transitory computer-readable storage medium having embodied thereon a program, which when executed by a computer causes the computer to execute a method, the method comprising:
setting a rotation axis on a basis of a pivot point and a point of interest on a subject, the pivot point serving as a fulcrum of a rod-shaped optical member whose observation optical axis is inclined with respect to a central axis and being not positioned on the observation optical axis;
setting a point on the optical member as the pivot point;
rotating the optical member around the rotation axis; and
rotating the optical member around the pivot point,
wherein the point on the optical member is set as the pivot point according to performance of a rotation operation by a user.

20. An imaging system comprising:
an imaging device including a rod-shaped optical member whose observation optical axis is inclined with respect to a central axis;
a rotation axis setting unit configured to set a rotation axis on a basis of a pivot point and a point of interest on a subject, the pivot point serving as a fulcrum of the optical member and being not positioned on the observation optical axis;
a pivot point setting unit configured to set a point on the optical member as the pivot point; and a posture control unit configured to
- rotate the optical member around the rotation axis, and
- rotate the optical member around the pivot point, wherein the point on the optical member is set as the pivot point according to performance of a rotation operation by a user, and wherein the rotation axis setting unit, the pivot point setting unit, and the posture control unit are each implemented via at least one processor.

* * * * *